(12) United States Patent
Lam et al.

(10) Patent No.: US 12,018,322 B2
(45) Date of Patent: Jun. 25, 2024

(54) AUTOCATALYTIC RELAY LOOP SIGNAL AMPLIFICATION MECHANISM AND APPLICATIONS THEREOF

(71) Applicant: Mobiusloop BioScience Limited, Hong Kong (CN)

(72) Inventors: Chung Wai Jonathan Lam, Hong Kong (CN); Chi Hang Wong, Hong Kong (CN); Chi Hang Wong, Hong Kong (CN)

(73) Assignee: Mobiusloop BioScience Limited, Hong Kong (CN)

( * ) Notice: Subject to any disclaimer, the term of this patent is extended or adjusted under 35 U.S.C. 154(b) by 68 days.

(21) Appl. No.: 17/646,819

(22) Filed: Jan. 3, 2022

(65) Prior Publication Data
US 2022/0235409 A1 Jul. 28, 2022

Related U.S. Application Data

(60) Provisional application No. 63/199,797, filed on Jan. 26, 2021.

(51) Int. Cl.
*C12Q 1/6844* (2018.01)
*C12Q 1/00* (2006.01)
*C12Q 1/6818* (2018.01)

(52) U.S. Cl.
CPC .......... *C12Q 1/6844* (2013.01); *C12Q 1/004* (2013.01); *C12Q 1/6818* (2013.01)

(58) Field of Classification Search
CPC .... C12Q 1/6818; C12Q 1/004; C12Q 1/6823; C12Q 2523/319
See application file for complete search history.

(56) References Cited

U.S. PATENT DOCUMENTS

| 7,358,052 | B2 | 4/2008 | Singh |
| 8,652,778 | B2 | 2/2014 | Bowman et al. |
| 8,735,167 | B2 | 5/2014 | Kutateladze et al. |
| 8,916,341 | B1 | 12/2014 | Bystryak et al. |

FOREIGN PATENT DOCUMENTS

| CN | 116134151 | * | 5/2023 | ....... G01N 33/54326 |
| WO | WO-2004007745 A2 | * | 1/2004 | ............. C09K 11/07 |

* cited by examiner

*Primary Examiner* — Thane Underdahl
(74) *Attorney, Agent, or Firm* — S&F/WEHRW

(57) ABSTRACT

Provided herein are methods involving an autocatalyzed looped relay amplification mechanism for detecting an analyte in a sample. The method is useful for detecting very low abundance analytes.

25 Claims, 20 Drawing Sheets
Specification includes a Sequence Listing.

A

B

A

DNA Sequence Releasing Moeity Covalently Attached to Spacer and Linker

B

DNA Sequence Releasing Moeity Covalently Attached to Photosensitizer via Spacer and Linker

C

DNA Sequence Targeting Moeity with Spacer and Linker

D

DNA Sequence Targeting Moeity Covalently Attached to Solid Substrate with Spacer and Linker (Not to Scale)

Diselenide

Ditelluride

Disulfide

Thioketal

Vinyl ether

Vinyl disulifde

Aminoacrylate

Peroxalate ester

Arylboronic ester

Anthracene

Oligoproline

AUTOCATALYTIC RELAY LOOP SIGNAL AMPLIFICATION MECHANISM AND APPLICATIONS THEREOF

CROSS-REFERENCE TO RELATED APPLICATIONS

This application claims priority from U.S. Provisional Patent Application No. 63/199,797, filed on Jan. 26, 2021, and PCT Application No. PCT/CN2021/141090, filed on 24 Dec. 2021, which are incorporated herein by reference in their entirety.

TECHNICAL FIELD

The present disclosure generally relates to the field of analytical chemistry. More particularly, the present disclosure relates to methods involving an autocatalyzed looped relay amplification mechanism for the detection of analytes, particularly analytes that may be present at extremely low abundance.

BACKGROUND

In the past decades, the demand for highly sensitive and specific analyte detections has grown to cater to the needs of the modern society, for examples clinical diagnosis, disease prevention, toxin detection, etc. Numerous novel detection techniques have been developed to achieve accurate quantification of analytes in environmental and biological samples. Some of these methods based on developing more sophisticated instrumentation to aid with detection, while some are based on replicating the analytes themselves to accumulate more signal for accurate detection. A well-known example is the amplification of targeted DNA sequence through polymerase chain reaction (PCR), or other more recent amplification techniques, such as ligase chain reaction (LCR), loop-mediated isothermal amplification (LAMP), etc. Despite the fact that these ingenious techniques are capable of extremely sensitive detection, they usually take hours to generate reliable results, require well-trained technicians, and expensive instruments and reagents.

Rather than directly detecting the analytes, some methods rely on replicating the product of a recognition event, which can usually be more easily detected. For instance, enzyme-linked immunosorbent assays (EILSA) are based on detecting the spectroscopic changes of the product from an enzymatic conversion. Some more recent examples make use of radical-initiated polymerization triggered by the recognition event to generate polymer in situ for signal amplification and detection. These techniques are more robust although the sensitivity is usually inferior.

Thus, there is a need in the art for a robust and highly sensitive detection method that can be fully automated without the need of labor intensive steps, laboratory facilities, and/or costly instruments.

SUMMARY

The current disclosure describes a mechanism design that can be triggered by the presence of an analyte that leads to a novel mechanism referred to herein as an "autocatalytic relay loop". The loop can go through a controllable positive-feedback loop to amplify a signal from the analytes exponentially, which can be detected and reaching the analyzable level.

In a first aspect, provided herein is a method for detecting an analyte in a sample suspected of containing the analyte, the method comprising:
(a) providing a conjugate substrate complex, wherein the conjugate substrate complex comprises a substrate comprising a plurality of targeting moieties bound via an optional first linker to a surface of the substrate; and a plurality of conjugates, wherein each of the plurality of conjugates comprises a releasing moiety covalently bonded via an optional second linker to a signal initiating agent, wherein each of the releasing moieties is reversibly bound to at least one of the plurality of targeting moieties and each of the plurality of targeting moieties is capable of selectively binding the analyte;
(b) providing a plurality of inactivated amplifying agents, wherein each inactivated amplifying agents comprises a masking group and an amplifying agent;
(c) providing a plurality of inactivated reporters;
(d) contacting the conjugate substrate complex and the sample, wherein in the presence of the analyte, one or more of the plurality of targeting moieties bind to the analyte causing the release of one or more of the plurality of conjugates from the conjugate substrate complex thereby forming one or more unbound conjugates;
(e) exciting the one or more unbound conjugates with a first excitation means whereby excitation of each of the one or more unbound the conjugate induces the signal initiating agent to emit an initiating signal;
(f) exposing a first inactivated amplifying agent to the initiating signal, whereby exposure of the first inactivated amplifying agent to the initiating signal induces at least one transformation selected from the group consisting of cleavage, chemical transformation, and electrical transformation of at least one of the first inactivated amplifying agent or the masking group from the first inactivated amplifying agent thereby forming the first amplifying agent;
(g) exciting the first amplifying agent with a second excitation means whereby excitation of the first amplifying agent induces the first amplifying agent to emit a relay signal, wherein the relay signal optionally induces at least one transformation selected from the group consisting of cleavage, chemical transformation, and electrical transformation of at least one of another inactivated amplifying agent or the masking group of another masked amplifying agent;
(h) repeating step (g) one or more times thereby forming a plurality of relay signals;
(i) exposing the plurality of inactivated reporters to the plurality of relay signals whereby exposure of the plurality inactivated reporters to the plurality of relay signals forms a plurality of activated reporters;
(j) exciting the plurality of activated reporters thereby emitting an amplified reporting signal;
(k) detecting the amplified reporting signal using a detection means; and
(l) determining based on the amplified reporting signal if the analyte is detected in the sample,
wherein the first excitation means and the second excitation means are the same or different; and wherein the initiating signal and the relay signal are the same or different.

In certain embodiments, exposure of the first inactivated amplifying agent to the initiating signal induces the cleavage of the masking group.

In certain embodiments, step (g) is repeated more than 100 times.

In certain embodiments, each of the plurality of targeting moieties comprises a deoxyribonucleic acid (DNA), ribonucleic acid (RNA), a peptide nucleic acid (PNA), an antibody, an antibody fragment, a peptide, a protein, or a small molecule.

In certain embodiments, the signal initiating agent comprises a photosensitizer, a nanoparticle, a protein, a luminescent agent, or a fluorescent agent.

In certain embodiments, the initiating signal and the relay signal are the same and selected from the group consisting of a small molecule, heat, light, or a combination thereof.

In certain embodiments, each of the initiating signal and the relay signal are singlet oxygen.

In certain embodiments, each of the plurality of conjugating agents comprise DNA, RNA, PNA, an antibody, an antibody fragment, a peptide, a protein, a small molecule, or a metal complex.

In certain embodiments, each of the plurality of targeting moieties comprises a single stranded DNA sequence and each of the plurality of releasing moieties comprise a substantially complimentary single stranded DNA sequence; or each of the plurality of targeting moieties comprise a single stranded RNA sequence and each of the plurality of releasing moieties each comprise a substantially complimentary single stranded RNA sequence.

In certain embodiments, the targeting moiety is covalently bonded via a first linker to the substrate, wherein the linker comprises a first nucleotide spacer comprising a first single stranded DNA spacer sequence or a first single stranded RNA spacer sequence.

In certain embodiments, the first DNA spacer sequence or the first single stranded RNA spacer sequence is between 2-10 nucleotides.

In certain embodiments, the signal initiating agent comprises a photosensitizer.

In certain embodiments, the plurality of conjugates are selected from the group consisting of:

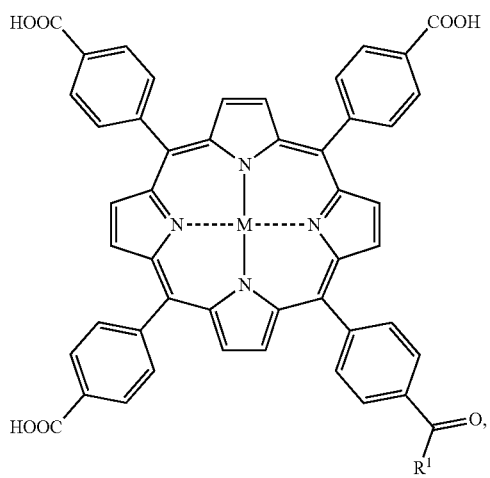

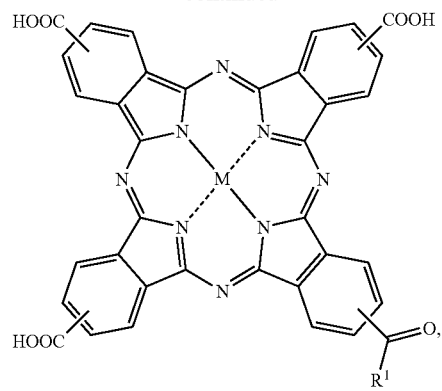

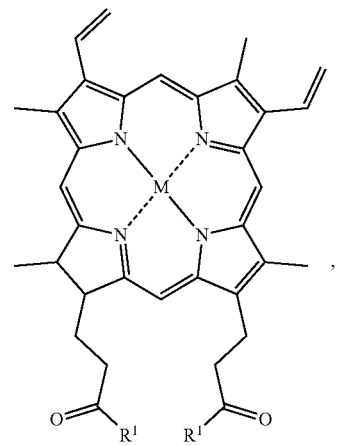

, and

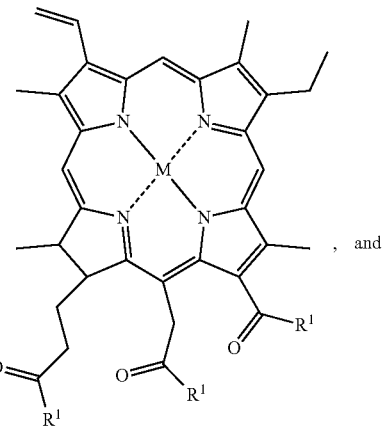

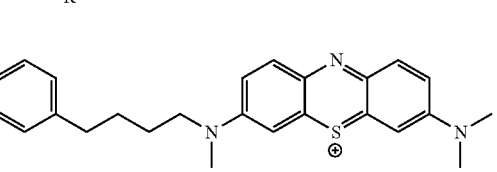

or a salt thereof, wherein $R^1$ is —X—Y or OH, wherein X is the linker, M is 2H or a non-paramagnetic metal, and Y is the releasing moiety, with the proviso that only one $R^1$ is —X—Y.

In certain embodiments, each of the initiating signal, the relay signal, and the plurality of relay signals is singlet oxygen.

In certain embodiments, the plurality of inactivated amplifying agents is selected from the group consisting of:

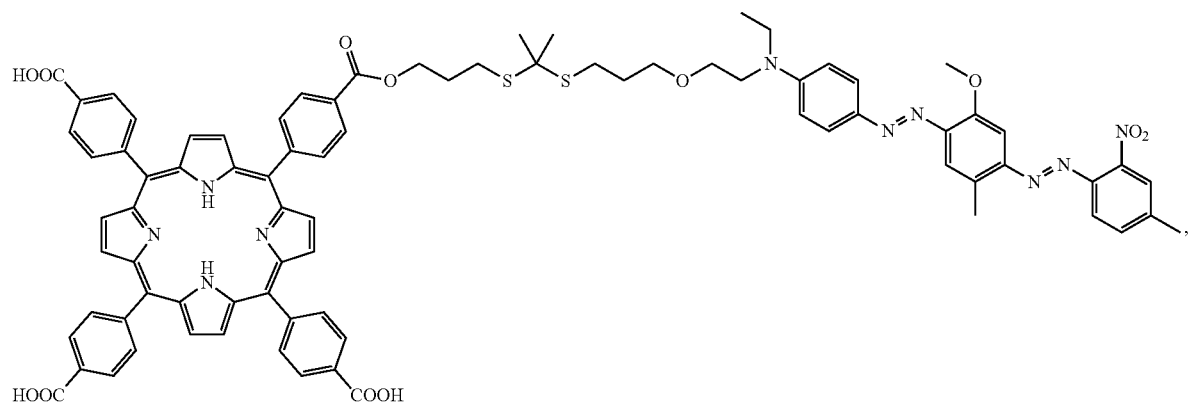
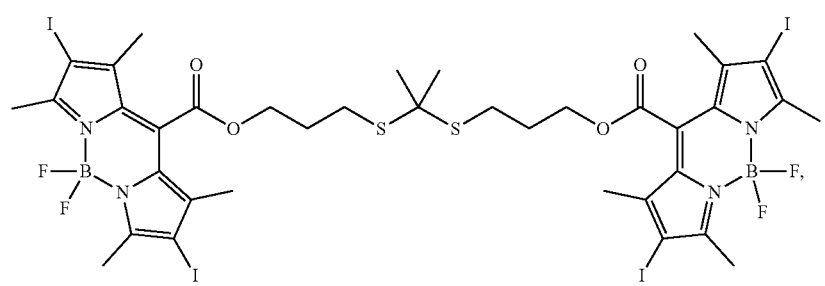
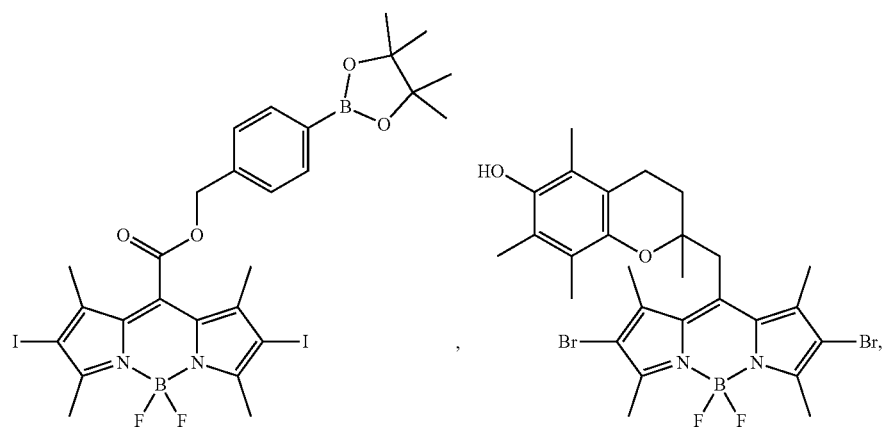
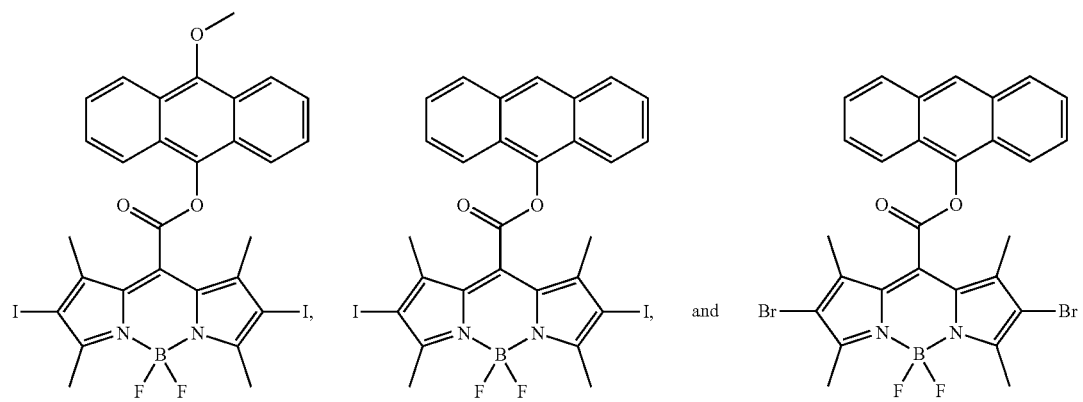
or a salt thereof.

In certain embodiments, the plurality of inactivated reporters have the structure:

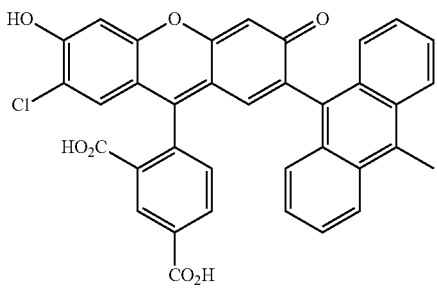 [SMILES: Cc1c2ccccc2c(-c2cc3c(-c4ccc(C(=O)O)cc4C(=O)O)c4cc(Cl)c(O)cc4oc-3cc2=O)c2ccccc12]

or a salt thereof.

In a second aspect, provided herein is a method for detecting a DNA analyte in a sample suspected of containing the DNA analyte, the method comprising:

(a) providing a conjugate substrate complex, wherein the conjugate substrate complex comprises a substrate comprising a plurality of DNA sequence targeting moieties bound via a first linker to a surface of the substrate; and a plurality of DNA conjugates, wherein each of the plurality of DNA conjugates comprise a conjugating DNA sequence moiety covalently bonded via a second linker to a photosensitizer, wherein each of the DNA sequence releasing moieties is reversibly bound to one of the plurality of DNA sequence targeting moieties and each of the plurality of DNA sequence targeting moieties is capable of selectively binding the analyte;

(b) providing a plurality of inactivated amplifying agents selected from the group consisting of:

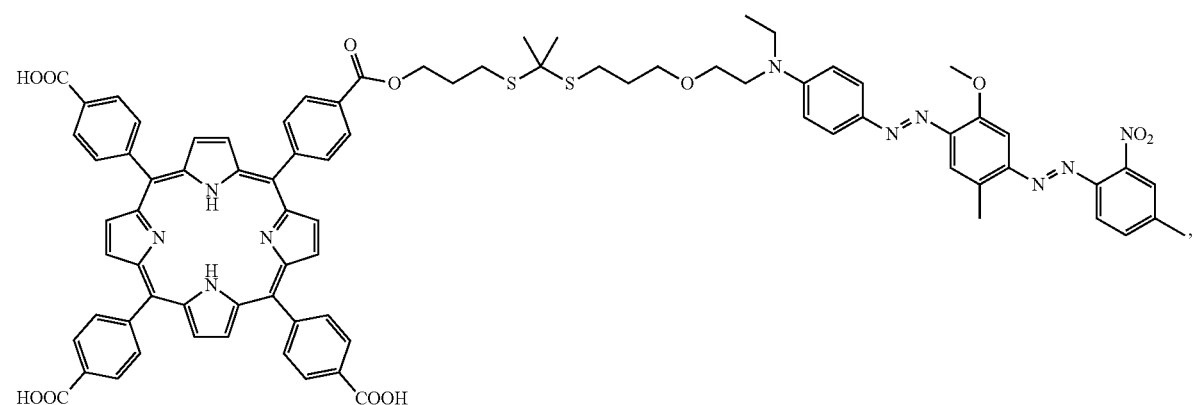

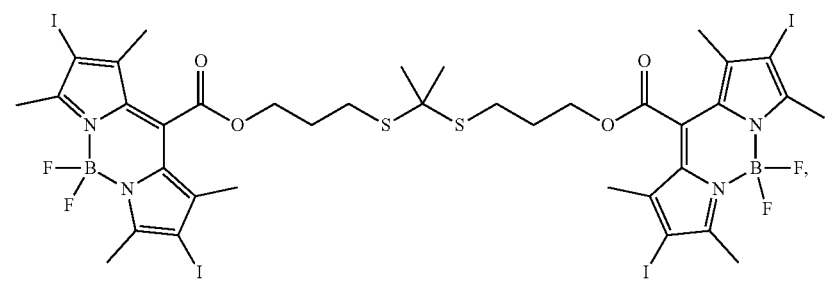

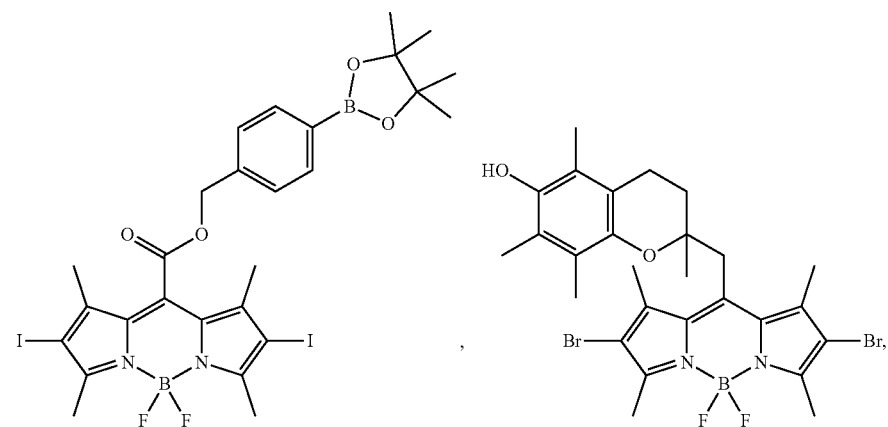

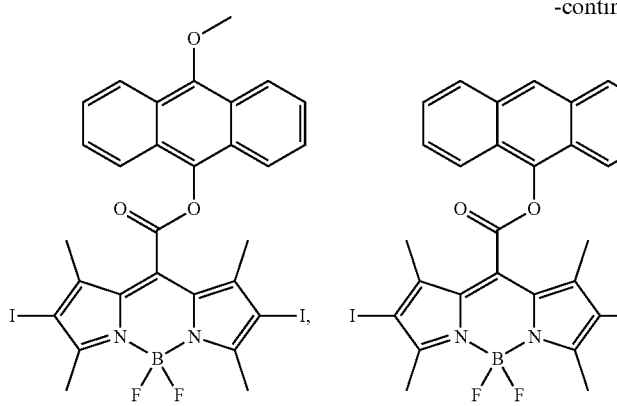 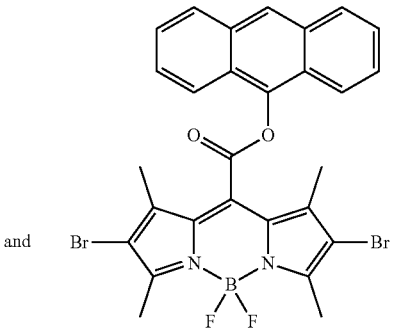

or a salt thereof, wherein each inactivated amplifying agent comprises a masking group and an amplifying agent;
(c) providing a plurality of inactivated reporters having the formula:

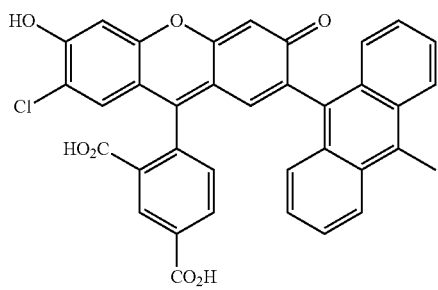 [SMILES: Cc1c2ccccc2c(-c2cc3c(-c4ccc(C(=O)O)cc4C(=O)O)c4cc(Cl)c(O)cc4oc-3cc2=O)c2ccccc12]

or a salt thereof;
(d) contacting the conjugate substrate complex and the sample, wherein in the presence of the analyte, one or more of the plurality of DNA sequence targeting moieties binds to the DNA analyte causing the release of one or more of the plurality of DNA conjugates from the conjugate substrate complex thereby forming one or more unbound DNA conjugates;
(e) irradiating the one or more unbound DNA conjugates with a first wavelength of light in the presence of triplet oxygen thereby producing singlet oxygen;
(f) exposing a first inactivated amplifying agent to the singlet oxygen, whereby exposure of the first inactivated amplifying agent to the singlet oxygen induces the cleavage of the masking group from the first inactivated amplifying agent thereby forming the first amplifying agent;
(g) irradiating the first amplifying agent with a second wavelength of light in the presence of triplet oxygen thereby producing singlet oxygen, wherein the amplified singlet oxygen optionally induces the release of the masking group of another masked amplifying agent;
(h) repeating step (g) one or more times thereby forming a plurality of singlet oxygen;
(i) exposing the plurality of inactivated reporters to the plurality of singlet oxygen whereby exposure of the plurality inactivated reporters to the plurality of singlet oxygen forms a plurality of activated reporters having the structure:

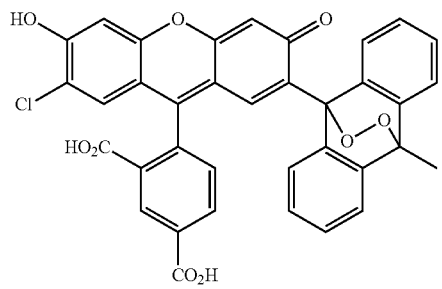 [SMILES: CC12OOC(c3cc4c(-c5ccc(C(=O)O)cc5C(=O)O)c5cc(Cl)c(O)cc5oc-4cc3=O)(c3ccccc31)c1ccccc12]

or a salt thereof;
j) irradiating the plurality of activated reporters with visible light thereby emitting an amplified reporting signal;
(k) detecting the amplified reporting signal using a spectrometer; and
(l) determining based on the amplified reporting signal if the analyte is detected in the sample In certain embodiments, the photosensitizer comprises a porphyrin, a phthalocyanine, a chlorin, a bacteriochlorin, a phenothiazinium, a xanthene, methylene blue, or a boron dipyrromethene (BODIPY).

In certain embodiments, each of the plurality of DNA conjugates has the formula:

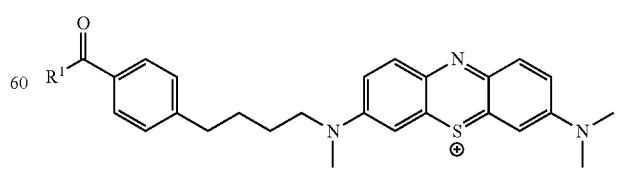

or a salt thereof, wherein $R^1$ is —X—Y or OH, wherein X is the linker and Y is the releasing moiety.

In certain embodiments, each of the plurality of DNA conjugates has the formula:

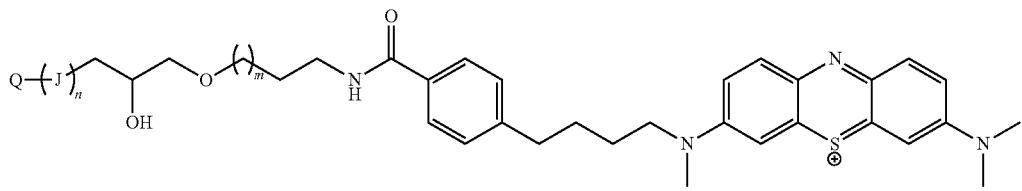

or a conjugate salt thereof, wherein m is a whole number selected from 0-2, n is a whole number selected from 3-5; J for each instance is a nucleotide independently selected from the group consisting of A, C, G, and T; and Q is the releasing moiety.

In certain embodiments, m is 0; N is 4; and each J is A.

In certain embodiments, the plurality of inactivated amplifying agents each have the structure:

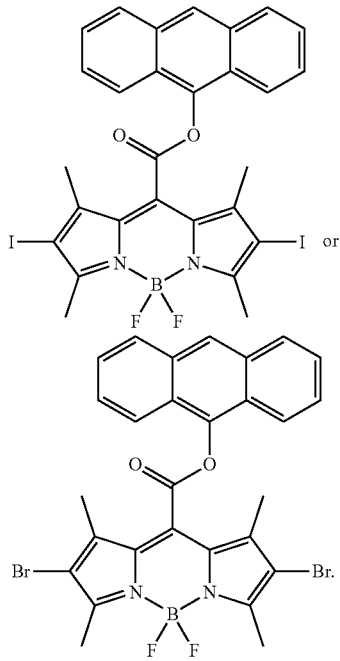

In certain embodiments, each of the plurality of DNA sequence targeting moieties comprises a polynucleotide sequence selected from the group consisting of: SEQ ID NO: 5, SEQ ID NO: 6, SEQ ID NO: 7, SEQ ID NO: 8, SEQ ID NO: 9, and SEQ ID NO: 10; and optionally a nucleotide spacer having between 2-10 nucleotides.

In a third aspect, provided herein is a method for detecting an analyte in a sample suspected of containing the analyte, the method comprising:
(a) providing a conjugate substrate complex, wherein the conjugate substrate complex comprises a substrate comprising a plurality of releasing moieties bound via an optional first linker to a surface of the substrate; and a plurality of conjugates, wherein each of the plurality of conjugates comprises a targeting moiety covalently bonded via an optional second linker to a signal initiating agent, wherein each of the targeting moieties is reversibly bound to at least one of the plurality of releasing moieties and each of the plurality of targeting moieties is capable of selectively binding the analyte;
(b) providing a plurality of inactivated amplifying agents, wherein each inactivated amplifying agents comprises a masking group and an amplifying agent;
(c) providing a plurality of inactivated reporters;
(d) contacting the conjugate substrate complex and the sample, wherein in the presence of the analyte, one or more of the of targeting moieties bind to the analyte causing the release of one or more of the plurality of conjugates from the conjugate substrate complex thereby forming one or more unbound conjugates;
(e) exciting the one or more unbound conjugates with a first excitation means whereby excitation of each of the one or more unbound the conjugate induces the signal initiating agent to emit an initiating signal;
(f) exposing a first inactivated amplifying agent to the initiating signal, whereby exposure of the first inactivated amplifying agent to the initiating signal induces at least one transformation selected from the group consisting of cleavage, chemical transformation, and electrical transformation of at least one of the first inactivated amplifying agent or the masking group from the first inactivated amplifying agent thereby forming the first amplifying agent;
(g) exciting the first amplifying agent with a second excitation means whereby excitation of the first amplifying agent induces the first amplifying agent to emit a relay signal, wherein the relay signal optionally induces at least one transformation selected from the group consisting of cleavage, chemical transformation, and electrical transformation of at least one of another inactivated amplifying agent or the masking group of another masked amplifying agent;
(h) repeating step (g) one or more times thereby forming a plurality of relay signals;
(i) exposing the plurality of inactivated reporters to the plurality of relay signals whereby exposure of the plurality inactivated reporters to the plurality of relay signals forms a plurality of activated reporters;
(j) exciting the plurality of activated reporters thereby emitting an amplified reporting signal;
(k) detecting the amplified reporting signal using a detection means; and
(l) determining based on the amplified reporting signal if the analyte is detected in the sample, wherein the first excitation means and the second excitation means are the same or different; and wherein the initiating signal and the relay signal are the same or different.

In certain embodiments, each of the plurality of conjugates is selected from the group consisting of:

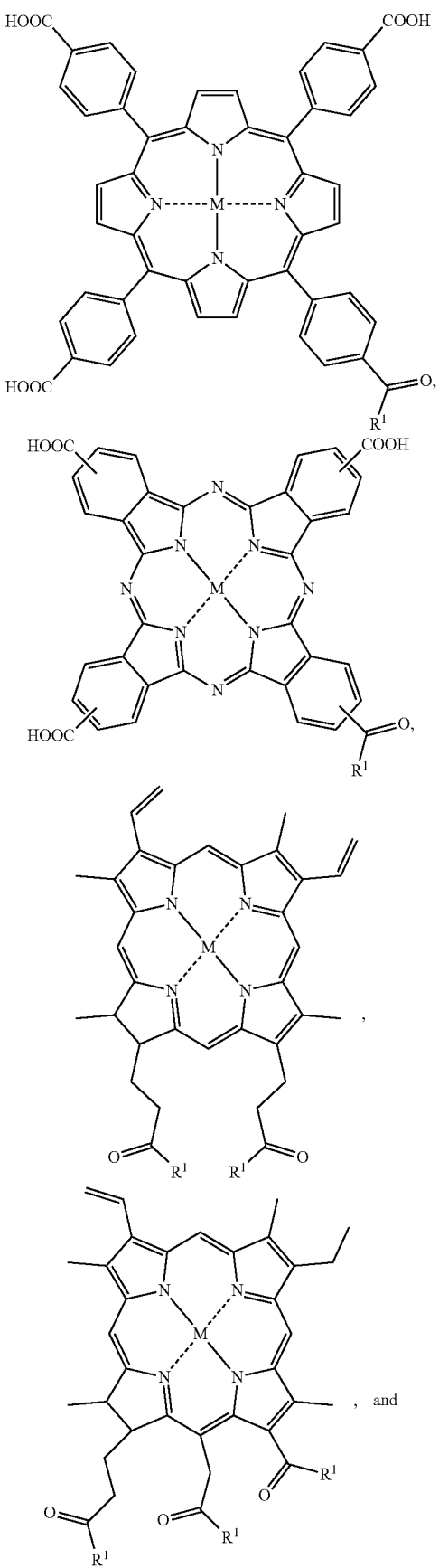

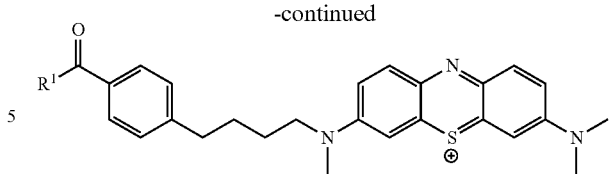

or a salt thereof, wherein $R^1$ is —X—$Y^1$ or OH, wherein X is the linker, M is 2H or a non-paramagnetic metal, and $Y^1$ is the targeting moiety, with the proviso that only one $R^1$ is —X—$Y^1$.

In certain embodiments, the method comprises an autocatalyzed looped relay amplification mechanism used for the detection of extremely low abundance analytes.

In certain embodiments, the signal initiating agent comprises any molecule capable of generating an initiating signal as described herein in response to excitation. Exemplary signal initiating agents include, but are not limiting to, dyes, probes, small molecules, proteins, nanoparticles, and metal-organic framework.

In certain embodiments, the signal initiating agent upon contacting the analyte can undergo excitation and/or a chemical reaction triggered by an external excitation, such as but not limited to a chemical, electric current, temperature, magnetic field, any form of energies, and electromagnetic radiation, thereby generating an initiating signal.

In certain embodiments, the initiating signal can be any molecule or signal, generated from the signal initiating agent that can trigger a chemical, physical, and/or electrical change of other components in the system, such inducing the cleavage of the masking group from the first inactivated amplifying agent.

In certain embodiments, the initiating signal can activate an inactivated amplifying agent in the system thereby generating an active amplifying agent.

In certain embodiments, the inactivated amplifying agent can be any molecule that is quenched, inactivated, masked, or inhibited by a functional group and/or its chemical structure.

In certain embodiments, the amplifying agent forms an autocatalytic-amplification loop to boost the initiating signal through the external excitation. The amplifying agent can further generate one or more relay signals to activate other inactivated amplifying agents to create a positive-feedback loop to generate a plurality of relay signals in an exponential manner upon stimulation by an external stimulant.

In certain embodiments, the plurality of relay signals generated from the amplifying agent in the system will lead to the activation of the plurality of inactivated reporters to become a plurality of activated reporters.

In certain embodiments, the plurality of activated reporters is any molecule including, but not limited to, fluorescent probes, nanoparticles, luminescent probes, proteins, and other substances that can be activated in the presence of the plurality of relay signals to generate an amplified reporting signal.

In certain embodiments, the amplified reporting signal is electromagnetic radiation, magnetic resonance, electric current, temperature, size, and conformation.

In certain embodiments, each loop, generate approximately 100-10,000-fold increase in the amount of the amplified reporting signal.

In certain embodiments, the number of loops the system can go through can be 1 to 10,000,000,000 times, depends on the concentration and efficiency of the silenced sensitizer-activated sensitizer pair.

In certain embodiments, all the components/reagents can be added in one-pot; or the components can be added in stepwise.

In certain embodiments, the method is performed at 0° C.-200° C.

In certain embodiments, the method is completed in 1-1,000 min.

In certain embodiments, the method is conducted by automation.

BRIEF DESCRIPTION OF THE DRAWINGS

The above and other objects and features of the present disclosure will become apparent from the following description of the disclosure, when taken in conjunction with the accompanying drawings.

DETAILED DESCRIPTION

Figure 1:
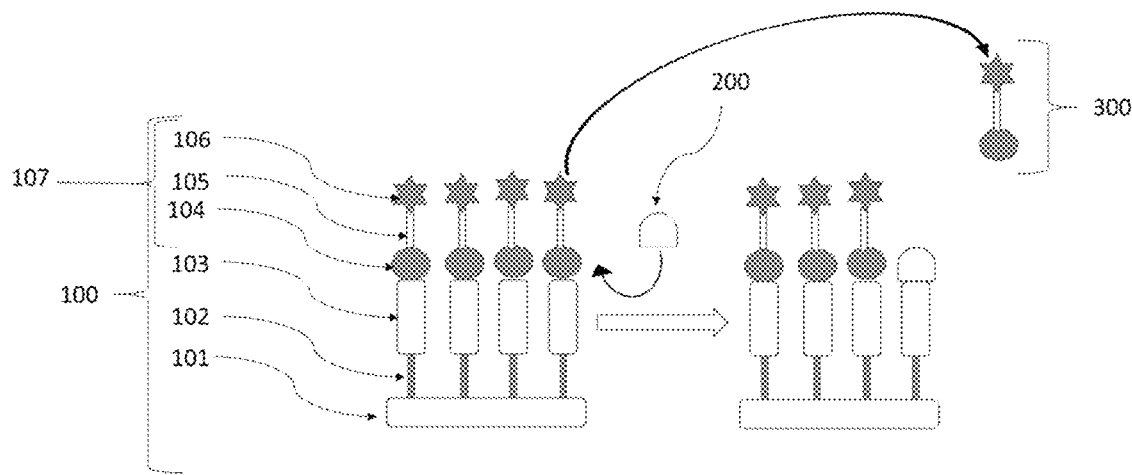
FIG. 1 depicts (A) an illustration showing the displacement of the conjugate (107) from the conjugate substrate complex (100) by the target analyte (200) thereby forming the unbound conjugate (300); and (B) depicts an illustration showing the displacement of the conjugate (108) from the conjugate substrate complex (100) by the target analyte (200) thereby forming the unbound conjugate (301) in accordance with certain embodiments described herein.
Figure 1:
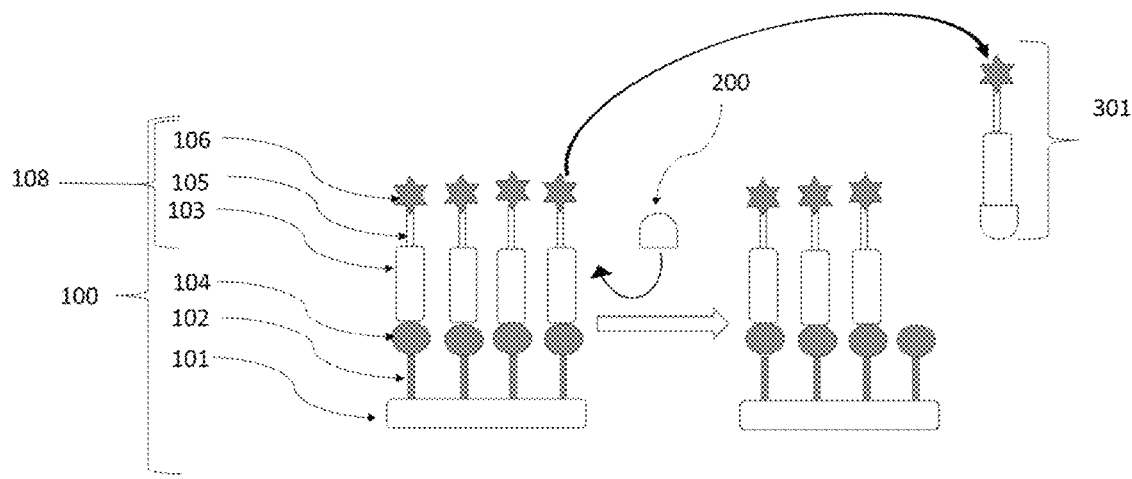

The present disclosures provide a method for detecting an analyte in a sample suspected of containing the analyte, the method comprising:

(a) providing a conjugate substrate complex, wherein the conjugate substrate complex comprises a substrate comprising a plurality of targeting moieties bound via an optional first linker to a surface of the substrate; and a plurality of conjugates, wherein each of the plurality of conjugates comprises a releasing moiety covalently bonded via an optional second linker to a signal initiating agent, wherein each of the releasing moieties is reversibly bound to at least one of the plurality of targeting moieties and each of the plurality of targeting moieties is capable of selectively binding the analyte;

(b) providing a plurality of inactivated amplifying agents, wherein each inactivated amplifying agents comprises a masking group and an amplifying agent;

(c) providing a plurality of inactivated reporters;

(d) contacting the conjugate substrate complex and the sample, wherein in the presence of the analyte, one or more of the plurality of targeting moieties bind to the analyte causing the release of one or more of the plurality of conjugates from the conjugate substrate complex thereby forming one or more unbound conjugates;

(e) exciting the one or more unbound conjugates with a first excitation means whereby excitation of the unbound conjugate induces the signal initiating agent to emit an initiating signal;

(f) exposing a first inactivated amplifying agent to the initiating signal, whereby exposure of the first inactivated amplifying agent to the initiating signal induces at least one transformation selected from the group consisting of cleavage, chemical transformation, and electrical transformation of at least of one of the first inactivated amplifying agent or the masking group from the first inactivated amplifying agent thereby forming the first amplifying agent;

(g) exciting the first amplifying agent with a second excitation means whereby excitation of the first amplifying agent induces the first amplifying agent to emit a relay signal, wherein the relay signal optionally induces at least one of cleavage, chemical transformation, and electrical transformation of at least one of another masked amplifying agent or the masking group of another masked amplifying agent;

(h) repeating step (g) one or more times thereby forming a plurality of relay signals;

(i) exposing the plurality of inactivated reporters to the plurality of relay signals whereby exposure of the plurality inactivated reporters to the plurality of relay signals forms a plurality of activated reporters;

(j) exciting the plurality of activated reporters thereby emitting an amplified reporting signal;

(k) detecting the amplified reporting signal using a detection means; and (l) determining based on the amplified reporting signal if the analyte is detected in the sample, wherein the first excitation means and the second excitation means are the same or different; and wherein the initiating signal and the relay signal are the same or different.

The term "sample" as used herein relates to a material or mixture of materials, typically, although not necessarily, in fluid form, but can also be in solid or gaseous form, suspected of containing the analyte. In certain embodiments, the sample are derived from a variety of sources such as from food stuffs, environmental materials (e.g., soil, air, water, and the like), or a biological such as a body fluid, a sample from a tissue or an organ, or a sample of wash/rinse fluid or a swab or smear obtained from an outer or inner body surface. In certain embodiments, samples of stool, urine, saliva, cerebrospinal fluid, blood, serum, plasma, or lacrimal fluid are encompassed as samples by the methods described herein.

The term "analyte", as used herein, generally refers to any specific substance or component that one is desirous of identifying, detecting, and/or measuring, e.g., in a chemical, physical, enzymatic, or optical analysis. An analyte can be an atom or molecule, or a collection of molecules. An analyte can be provided in a sample that is suspected of containing the analyte. Analytes of interest include, for example, antigens (such as antigens specific to bacterial, viral or protozoan organisms); antibodies, particularly those induced in response to an infection, allergic reaction, or vaccine; hormones, proteins and other physiological substances (for example, human chorionic gonadotropin, estrogens, progestins, testosterones, corticosteroids, human growth factors, hemoglobin, and cholesterol); a polynucleotide, particularly those implicated in a disease state or health condition; a variety of enzymes; therapeutic compounds and illicit drugs; contaminants and environmental pollutants; or any number of natural or synthetic substances. As is appreciated by one skilled in the art, the number of natural and synthetic substances which can be detected by the assay devices and methods of the present invention is extensive, and all such substances are contemplated by the present disclosure.

FIG. 1A provides an exemplary illustration showing the structure the conjugate substrate complex and the formation of the unbound conjugate in accordance with certain embodiments described herein. In reference to FIG. 1A, the conjugate substrate complex (100) comprising a plurality of targeting moieties (103), each targeting moiety (103) bound to the substrate (101) via an optional first linker (102); and a plurality of conjugates (107), each conjugate (107) comprising the releasing moiety (104) bound via optional second linker (105) to the signal initiating moiety (106). In the presence of the analyte (200), one or more of the plurality of conjugates (107) can be displaced when the analyte (200) binds to one or more of the plurality of targeting moieties (103) thereby forming the unbound conjugate (300).

The method described herein can be conducted using a substrate, such as a solid support. The substrate can be used to bind and immobilize the conjugate on the plurality of targeting moieties. Use of the solid support may further improve the selectivity of the method by reducing unwanted background initiating signal produced by conjugate. The substrate can take any shape including, but not limited to, a microsphere, bead, or particle, a planar structure, such as a slide, chip, microchip and/or array, a non-planar, such as the inner or outer surface of a tube or vessel, a rod, a cone, a disk, and a cube.

In certain embodiments, the substrate comprises a material selected from the group consisting of a polymer, a ceramic, a semiconductor, and a metal. The metal can be ferromagnetic. Exemplary substrates include, but are not limited to, gold, polystyrene, siloxanes, silicon dioxide, a polymethacrylate, a polyacrylate, polystyrene, polyurethanes, polypropylenes, polyvinyl chloride, polyesters, polyethers, and polyethylene, gold, silver, platinum, aluminum, palladium, copper, cobalt, indium, nickel, ZnS, ZnO, Ti, $TiO_2$, Sn, $SnO_2$, Si, $SiO_2$, Fe, $Fe^{4+}$, FeO, $Fe_2O_3$, $Fe_3O_4$, Ag, and the like.

In certain embodiments, after the conjugate substrate complex is brought in contact with the sample, excess conjugate substrate complex and/or conjugate substrate complex, which has at least partially reacted with the analyte can optionally be separated from the sample using any conventional method, such as by filtration, flowing the sample past the conjugate substrate complex, etc. Separation of excess conjugate substrate complex and/or conjugate substrate complex, which has at least partially reacted with the analyte can reduce unintended activation of the signal initiating agent(s) in the bound conjugate(s).

In instances in which the substrate is a ferromagnetic metal, after the conjugate substrate complex is brought in contact with the sample, excess conjugate substrate complex and/or conjugate substrate complex, which has at least partially reacted with the analyte can optionally be separated from the sample using a magnet.

The plurality of targeting moieties bound via an optional first linker to a surface of the substrate can be bound via a covalent bond, ionic interactions, and/or complexation to at least one surface of the substrate.

In certain embodiments, the analyte is selected from a polynucleotide selected from DNA and RNA, a peptide, a protein, and a small molecule. In certain embodiments, the analyte is a polynucleotide having 10-80 nucleotides.

In certain embodiments, the analyte comprises a nucleotide sequence that substantially complimentary to a sequence selected from the group consisting of SEQ ID NO: 5; SEQ ID NO: 6; SEQ ID NO: 7, SEQ ID NO: 8, SEQ ID NO: 9, and SEQ ID NO: 10.

The targeting moiety can selectively bind to a specific analyte of interest, e.g., a polynucleotide, lipid, polypeptide, carbohydrate, small molecule, metal, etc. The targeting moiety can be a polynucleotide selected from DNA and RNA, PNA, an antibody, an antibody fragment (such as Fab, Fab', F(ab') 2, and Fv), single chain (ScFv)) a peptide, an aptamer, or a small molecule that is capable of selectively binding to a target of interest, such as a carbohydrate, polynucleotide, lipid, polypeptide, protein, small molecule, cellular receptor, etc. Covalent conjugation of the substrate via an optional first linker to the targeting moiety can be accomplished using well known methods known by the skilled person. In certain embodiments, the targeting moiety is selected from the group consisting of a polynucleotide selected from DNA and RNA, PNA, a peptide, an antibody, an antibody fragment, a protein, or a small molecule. In certain embodiments, the targeting moiety is a DNA targeting moiety comprising a nucleotide sequence.

In certain embodiments, the targeting moiety is linked to the substrate agent via a first linker. The first linker may contain functional groups, for example to serve as attachment sites for the targeting moiety and the substrate. Preferably, the length, structure, and attachment site of the first linker do not substantially interfere with the targeting moiety's ability to reversibly bind the releasing moiety or the analyte. Suitable first linkers are well known to those of skill in the art and include, but are not limited to, straight or branched-chain carbon linkers optionally substituted with ester, carbonate, carbamate, amide, urea, amine, ether, functionality in the backbone and/or side chain of the linker, heterocyclic carbon linkers optionally substituted with ester, carbonate, carbamate, amide, urea, amine, ether, functionality in the backbone and/or side chain of the linker, peptide linkers, nucleotide linkers. In certain embodiments, the first linker can be presented by the formula: *—(CH$_2$)CH(OH)(CH$_2$)O(CH$_2$)$_m$NH—**, wherein m is a whole number selected from 2-10; 2-8; 2-6; 2-4 or 2-3; * represents the attachment site to the substrate, which can be done via an optional substrate linker (the substrate linker can be the same or different as the first linker); and ** represents the targeting moiety.

In certain embodiments, the first linker further comprises a first nucleotide spacer and an optionally substituted straight chain carbon linker. The first nucleotide spacer can comprise a non-binding sequence having between 2-20 nucleotides. In certain embodiments, the first nucleotide spacer comprises a non-binding sequence having between 2-15, 2-10, 3-10, 3-8, 3-6, or 4-6 nucleotides. The first nucleotide spacer can comprise any combination of naturally occurring and/or non-naturally occurring nucleotides. In certain embodiments the first nucleotide spacer has between 1-10, 3-10, 3-7, or 4-6 adenine nucleotides.

The signal initiating agent can comprise any substance that is capable of producing a detectable signal. Exemplary signal initiating agents suitable for use in the methods described herein include, but are not limited to, fluorescent agents, chemiluminescent agents, catalysts, enzymes, enzymatic substrates, dyes, compounds of generating energetic molecules (such as singlet oxygen) colloidal metallic and nonmetallic particles, and organic polymer latex particles. In certain embodiments, the signal initiating agent s comprises a photosensitizer, a nanoparticle, a protein, a luminescent agent, or a fluorescent agent.

In certain embodiments, the signal initiating agent comprises a photosensitizer selected from the group consisting of a phthalocyanine, a porphyrin derivative, a purpurin derivative, a psoralen derivative, a bergapten derivative, an angelicin derivative, a chlorin derivative, a flavin derivative, a tetraphenylporphyrin derivative, a benzoporphyrin derivative, a boron dipyrromethene derivate, a ruthenium(II) complex, a purpurine derivative, a porphycene, a pheophorbide and their metal complexes, a copper (II) phthalocyanine, acridine orange, a phthalocyanine, methylene blue, rose bengal, a tetraphenylethene derivative, a fullerene, a naphthalocyanine, a texaphyrin, a gold nanorod, and 5-aminolevulinic acid.

In certain embodiments, signal initiating agent comprises a photosensitizer selected from the group consisting:

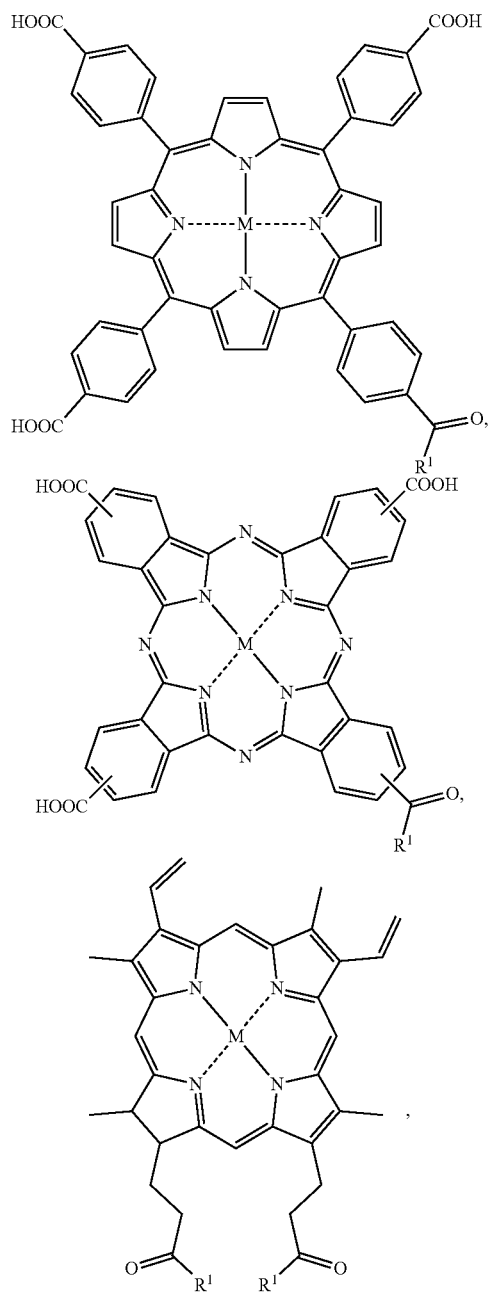

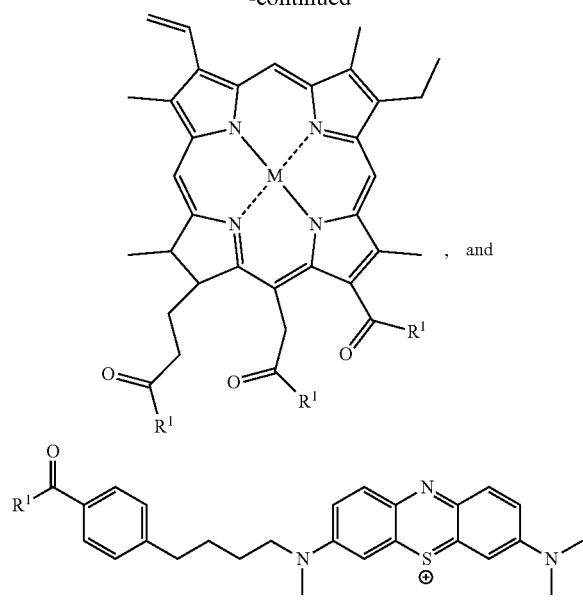

, and

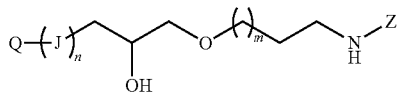

or a salt thereof, wherein $R^1$ is —X—Y or OH, wherein X is the second linker, M is 2H or a non-paramagnetic metal, and Y is the releasing moiety, with the proviso that only one $R^1$ is —X—Y. In certain embodiments, M is 2H, $Al^{3+}$, $Ga^{3+}$, Si, $Pd^{2+}$, $Pt^{2+}$, or $Zn^{2+}$.

In certain embodiments, the releasing moiety is linked to the signal initiating agent via a second linker. The second linker may contain functional groups, for example to serve as attachment sites for the releasing moiety and the signal initiating agent. Preferably, the length, structure, and attachment sites of the second linker do not substantially interfere with the releasing moiety's ability to reversibly bind the targeting moiety and the signal initiating agent's agent ability to produce an initiating signal. Suitable second linkers are well known to those of skill in the art and include, but are not limited to, straight or branched-chain carbon linkers optionally substituted with ester, carbonate, carbamate, amide, urea, amine, ether, functionality in the backbone and/or side chain of the linker, heterocyclic carbon linkers optionally substituted with ester, carbonate, carbamate, amide, urea, amine, ether, functionality in the backbone and/or side chain of the linker, peptide linkers, nucleotide linkers. In certain embodiments, the second linker can be presented by the formula: *—$(CH_2)CH(OH)(CH_2)_2O(CH_2)_m$NH—**, wherein m is a whole number selected from 2-10; 2-8; 2-6; 2-4 or 2-3; * represents the releasing moiety; and ** represents the initiating agent.

In certain embodiments, the second linker further comprises a second nucleotide spacer and an optionally substituted straight chain carbon linker. The second nucleotide spacer can comprise a non-binding sequence having between 2-20 nucleotides. In certain embodiments, the second nucleotide spacer comprises a non-binding sequence having between 2-15, 2-10, 3-10, 3-8, 3-6, or 4-6 nucleotides. The second nucleotide spacer can comprise any combination of naturally occurring and/or non-naturally occurring nucleotides. In certain embodiments the second nucleotide spacer has between 1-10, 3-10, 3-7, or 4-6 adenine nucleotides.

In certain embodiments, each of the plurality of conjugates are represented by the formula:

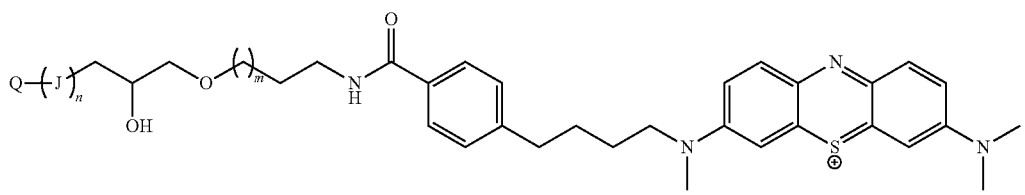

or a conjugate salt thereof, wherein m is a whole number selected from 0-6, 0-4, 0-3, 0-2, n is a whole number selected from 0-6; 1-6; 2-6; 2-5; 3-5; J for each instance is a nucleotide independently selected from the group consisting of A, C, G, and T; Q is the releasing moiety; and Z is the signal initiating agent. In certain embodiments, m is 0-2; n is 4-6; the targeting moiety is DNA; and the signaling agent is a photosensitizer.

In certain embodiments, each of the plurality of conjugates are represented by the formula:

or a conjugate salt thereof, wherein m is a whole number selected from 0-6, 0-4, 0-3, 0-2, n is a whole number selected from 0-6; 1-6; 2-6; 2-5; 3-5; J for each instance is a nucleotide independently selected from the group consisting of A, C, G, and T; and Q is the targeting moiety. In certain embodiments, m is 0-2; n is 4-6; and the releasing moiety is DNA. In certain embodiments, each of the plurality of conjugates have the structure depicted in FIG. 2B.

As set out herein, certain embodiments of the compounds described herein may contain a cationic moiety, such as an iminium, or a basic functional group, such as amino, and are, thus, capable of forming salts with acids. Representative salts include the bromide, chloride, sulfate, bisulfate, carbonate, bicarbonate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like.

The salts of the compounds of the present disclosure include salts or quaternary ammonium salts of the compounds, e.g., from organic or inorganic acids. For example, such salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds described herein may contain one or more acidic functional groups and, thus, are capable of forming salts with bases. Representative salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

Figure 2:
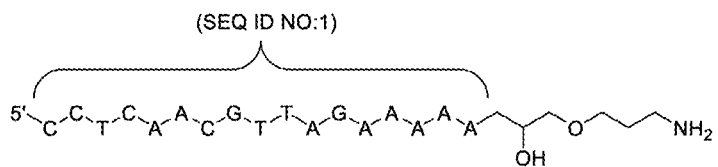
FIG. 2 depicts (A) the structure of an exemplary DNA sequence releasing moiety (SEQ ID NO: 1) attached to via a 1-(3-aminopropoxy)propanyl-2-ol first linker according to certain embodiments described herein; (B) the structure of an exemplary DNA sequence conjugate comprising modified methylene blue (MB) covalently bonded via a 1-(3-aminopropoxy)propanyl-2-ol first linker to an exemplary DNA sequence releasing moiety (SEQ ID NO: 1) attached to 1-(3-aminopropoxy)propanyl-2-ol first linker according to certain embodiments described herein; and (C) structure of an exemplary DNA sequence targeting moiety (SEQ ID NO: 2) attached to 1-(3-aminopropoxy)propanyl-2-ol second linker according to certain embodiments described herein. (D) the structure of an exemplary DNA-modified iron oxide particle (IOP) comprising carboxyl-decorated IOP covalently bonded via a 1-(3-aminopropoxy)propanyl-2-ol first linker to an exemplary DNA sequence targeting moiety (SEQ ID NO: 2) attached to 1-(3-aminopropoxy)propanyl-2-ol first linker according to certain embodiments described herein.
Figure 2:
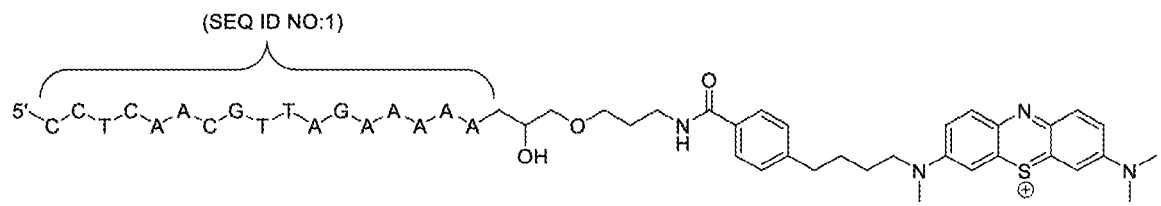
Figure 2:
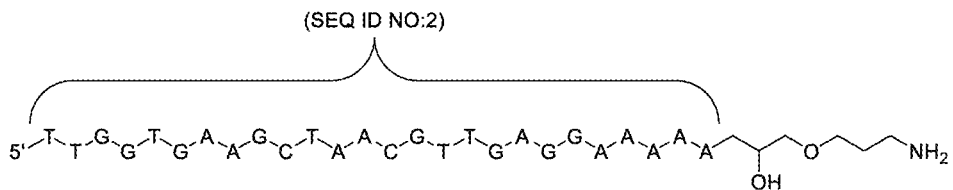
Figure 2:
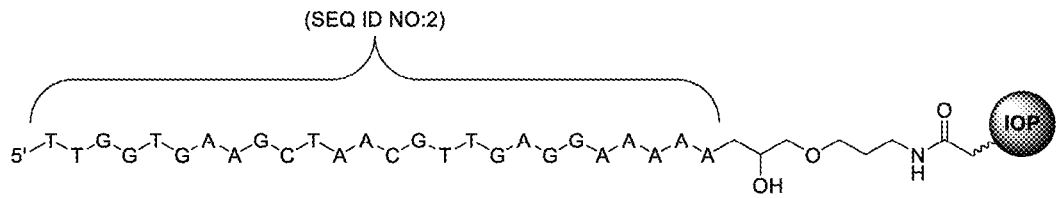

FIG. 2 depicts an exemplary 21-base DNA sequence targeting moiety (FIG. 2D, SEQ ID NO: 2) covalently bonded to a TOP via a linker and nucleotide spacer; and a 12-base DNA sequence releasing moiety covalently bonded to a photosensitizer via a nucleotide spacer and linker (FIG. 2B, with SEQ ID NO: 1), which may be pre-complexed to the DNA targeting moiety as it is complementary to a section of the 21-base targeting DNA sequence (SEQ ID NO: 2) (thereby forming the conjugate substrate complex). The target DNA analyte would be a DNA sequence that is complementary to the whole section of the 21-base DNA sequence targeting moiety. During the detection, the target DNA analyte displaces the pre-complexed DNA releasing moiety with photosensitizer as the binding strength of the target DNA analyte will be higher than that of the DNA sequence releasing moiety with photosensitizer. The thus unbound DNA conjugate moiety can be freed in the medium and be used as the unbound conjugate in the loop to generate the initiating signal.

When the conjugate substrate complex is brought into contact with the analyte, the targeting moiety can bind the analyte thereby forming a targeting moiety analyte complex and freeing the unbound conjugate from the conjugate substrate complex.

In certain embodiments, the releasing DNA sequence is 100% complementary to the DNA sequence targeting moiety, while in other aspects, the individual oligonucleotides are at least (meaning greater than or equal to) about 95% complementary to each over the all or part of length of each oligonucleotide, at least about 90%, at least about 85%, at least about 80%, at least about 75%, at least about 70%, at least about 65%, at least about 60%, at least about 55%, at least about 50%, at least about 45%, at least about 40%, at least about 35%, at least about 30%, at least about 25%, at least about 20% complementary to each other.

The term "substantially complimentary" as used herein means a sequence that is 100%, at least 95%, at least about 90%, at least about 85%, at least about 80%, at least about 75%, at least about 70%, at least about 65%, at least about 60%, at least about 55%, at least about 50%, at least about 45%, at least about 40%, at least about 35%, at least about 30%, at least about 25%, or at least about 20% complementary to another sequence over the all or part of length of each sequence.

The binding affinity of the analyte to the targeting moiety can generally be greater than the binding affinity of the releasing moiety to the targeting moiety. In certain embodiments, the binding affinity of the analyte to the targeting moiety is 2×, 5×, 10×, 100×, 1,000×, 10,000×, 100,000×, 1,000,000× or higher than the binding affinity of the releasing moiety to the targeting moiety. In certain embodiments, the binding affinity of the analyte to the targeting moiety is 2-1,000,000 times stronger, 2-500,000 times stronger, 2-250,000 times stronger, 2-100,000 times stronger, 2-50,000 times stronger, 2-10,000 times stronger, 2-1,000 times stronger, or 100-1,000 times stronger than the binding affinity of the releasing moiety to the targeting moiety.

The unbound conjugate can be excited using a first excitation means. The first excitation means for exciting the unbound conjugate can depend on the nature of the signal initiating agent. The selection of a suitable first excitation means can be readily accomplished by a skilled person. Exemplary first excitation means include, but are not limited to, a chemical, electric current, heat, magnetic field, electromagnetic radiation, nuclear radiation, ultrasound, and any other form of energy. In certain embodiments, the first excitation means is electromagnetic radiation selected from the group consisting of gamma rays, X-rays, ultraviolet, visible, infrared, microwave, radio waves, and combinations thereof.

In certain embodiments, the first excitation means is visible light having a wavelength between 400-700 nm. In certain embodiments, the first excitation means is visible light between 400-650 nm, 400-600 nm, 400-550 nm, 400-500 nm, 400-450 nm, 410-440 nm, or 410-430 nm.

Excitation of the unbound conjugate with a first excitation means induces the signal initiating agent to emit an initiating signal. The initiating signal can be a small molecule, a radical, an oxidizing agent, a reducing agent, heat, light, or a combination thereof.

In instances in which the unbound conjugate comprises a photosensitizer, excitation of the photosensitizer in the presence of triplet oxygen produces a signal, wherein the signal is singlet oxygen.

In certain embodiments, the inactivated amplifying agent comprises a masking group that inhibits the function of the amplifying agent. The masking group can take any form, such as a protecting group on the inactivated amplifying agent that can be cleaved upon exposure to the initiating signal or relay signal; a chemically active site in the inactivated amplifying agent that undergoes a chemical transformation upon exposure to the initiating signal or relay signal; a redox active site in the inactivated amplifying agent that upon exposure to the initiating signal or relay signal can be oxidized or reduced; an electrically active site in the inactivated amplifying agent that upon exposure to the initiating signal or relay signal can be modified (e.g., by excitation of an electron); and/or a conformational/vibrational transition that occurs upon exposure to the initiating signal or relay signal.

In certain embodiments, the inactivated amplifying agent comprises a masking group that undergoes cleavage upon exposure to the initiating signal or relay signal. In certain embodiments, the inactivated amplifying agent comprises a masking group that undergoes cleavage upon exposure to the initiating signal or relay signal, wherein the initiating signal and relay signal are singlet oxygen.

The first inactivated amplifying agent can then be exposed to the initiating signal, whereby exposure of the first inactivated amplifying agent to the initiating signal induces the formation of the first amplifying agent.

The first inactivated amplifying agent can be any compound that upon exposure to the initiating signal triggers a chemical, physical, and/or electrical change thereby generating the first activated amplifying agent.

In certain embodiments, the chemical change comprises cleavage of the masking group from the first inactivated amplifying agent thereby forming the first amplifying agent.

Figure 22:
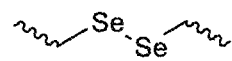
FIG. 22 depicts exemplary reactive oxygen species (ROS)-responsive chemical structures in some inactivated amplifying agents.
Figure 22:
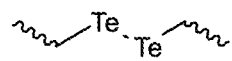
Figure 22:
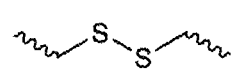
Figure 22:
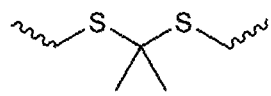
Figure 22:
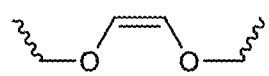
Figure 22:
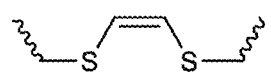
Figure 22:
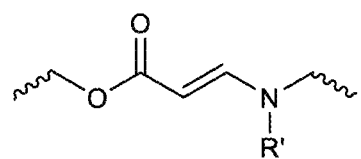
Figure 22:
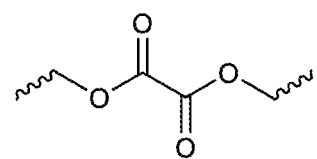
Figure 22:
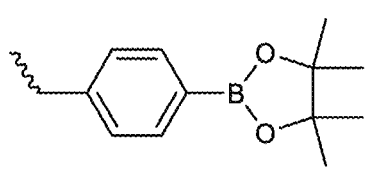
Figure 22:
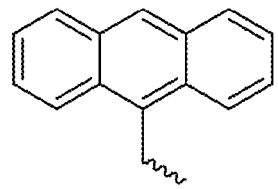
Figure 22:
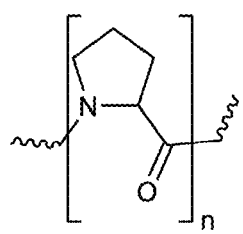

The masking group can comprise a ROS-responsive chemical structure, which is capable of undergoing a chemical or electrical reaction with ROS thereby resulting in cleavage of the masking group. Examples of ROS-responsive chemical structures include, but are not limited to diselenides, ditellurides, disulfides, thioketals, thioacetals, vinyl ethers, vinyl disulfides, aminoacrylates, peroxalate esters, arylboronic esters, anthracenes, and oligoprolines (FIG. 22).

In certain embodiments, the first inactivated amplifying agent is selected from the group consisting of:

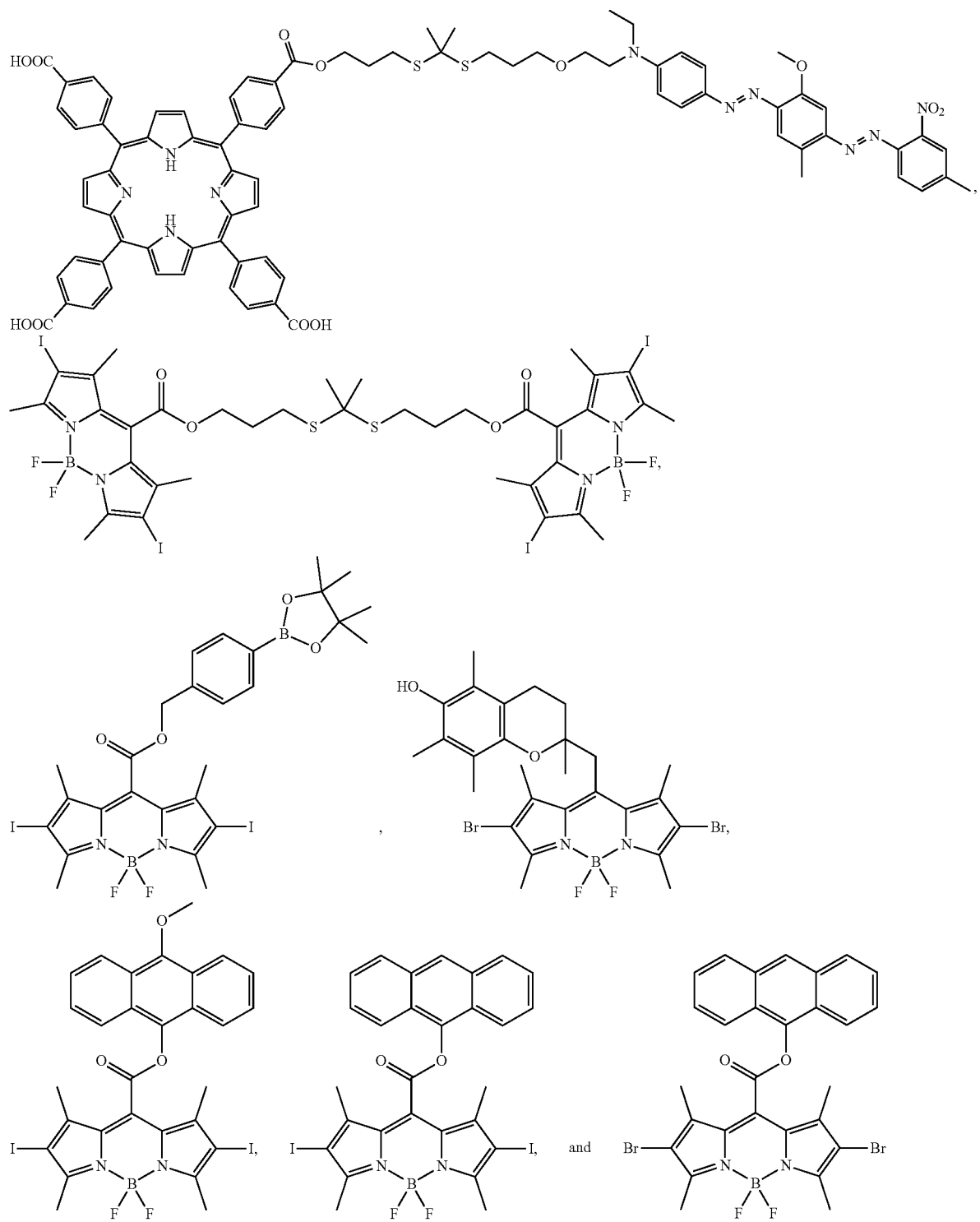

or a salt thereof.

Although a high concentration of inactivated amplifying agent may result in undesirable amplification of the initiating signal and/or relay signal due to the intrinsic minimal signal (e.g., a radical initiating signal and/or relay signal) generation efficiency of an inactivated amplifying agent, such as a quenched photosensitizer, it was surprisingly discovered that there is a critical minimum concentration of the inactivated amplifying agent that the system requires in order for the autocatalytic amplification to be able to function. This is due to the lifetime and the effective diffusion distance of the initiating signal and/or relay signal (e.g., a radical initiating signal and/or relay signal) used in the autocatalytic system in a particular solvent. If the concentration of the inactivated amplifying agent is too low such that the resulting intermolecular distance between reactive components is larger than the maximum diffusion distance of the initiating signal and/or relay signal (e.g., a radical initiating signal and/or relay signal), the autocatalytic cycle may not propagate and sustain. For example, singlet oxygen has a lifetime of a few microseconds, which can convert to a diffusion distance of tens or hundreds of nanometers. The corresponding critical concentration for an inactivated amplifying agent that responds to singlet oxygen may less than 50 μM. In certain embodiments, the concentration of the inactivated amplifying agent is between 1-50,000 nM, 1-10,000 nM, 1-1,000 nM; 1-900 nM; 1-800 nM; 1-700 nM; 1-600 nM; 1-500 nM; 1-400 nM; 1-300 nM; 1-200 nM; 1-150 nM; 1-100 nM, 75-125 nM.

In certain embodiments, the amplifying agent is selected from the group consisting of:

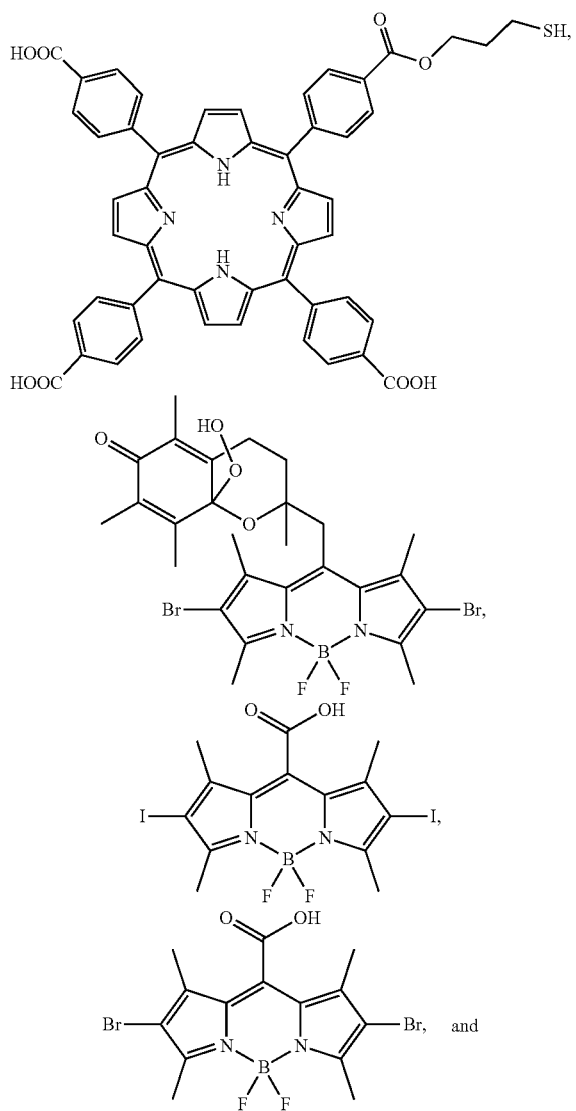

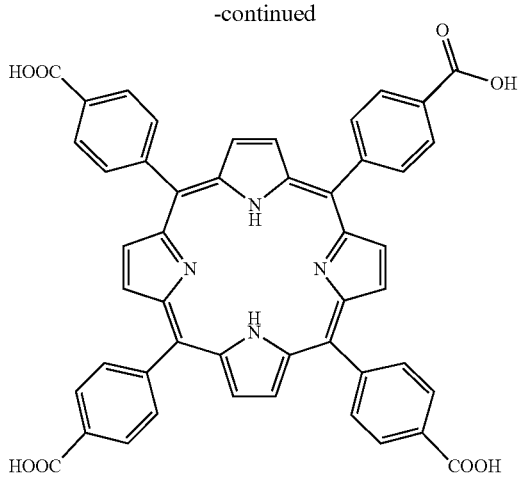

or a salt thereof.

Figure 3:
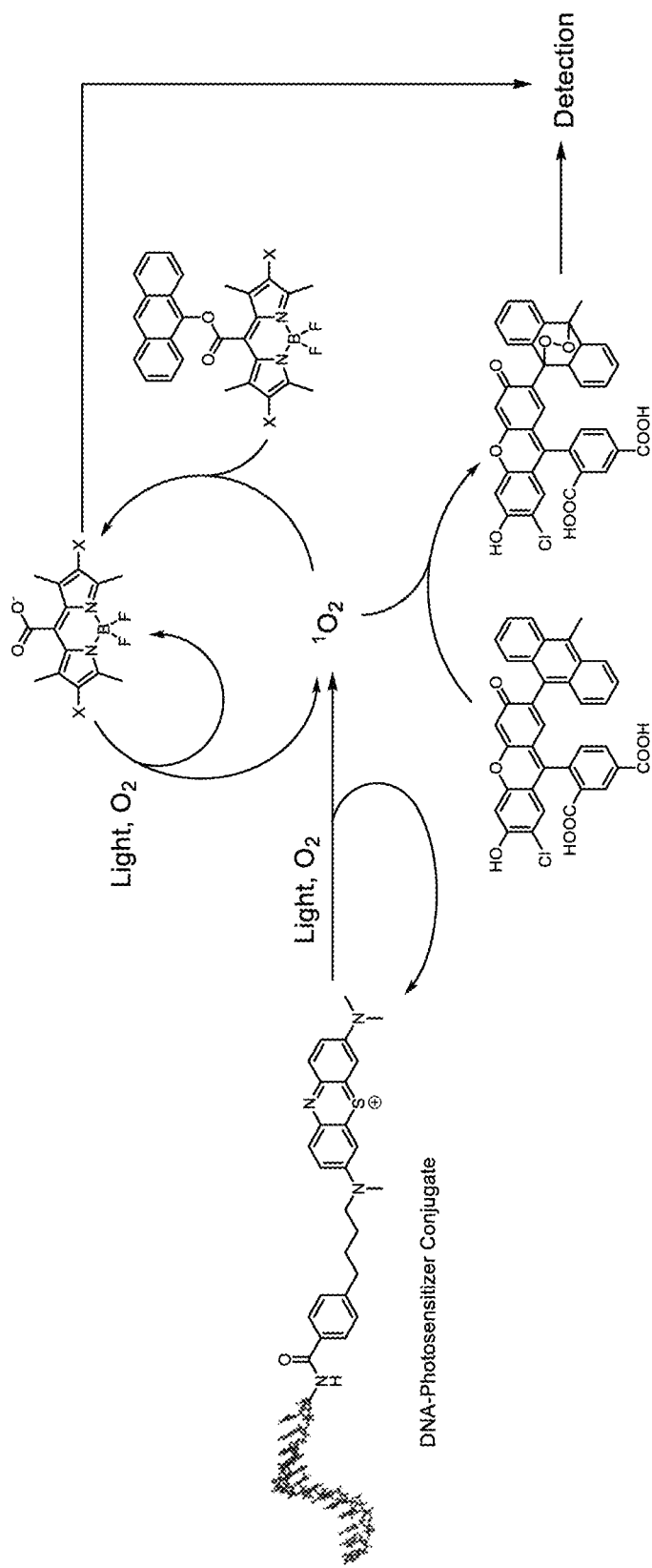
FIG. 3 depicts an exemplary scheme showing the present Autocatalytic Relay Loop design and mechanism.
Figure 21:
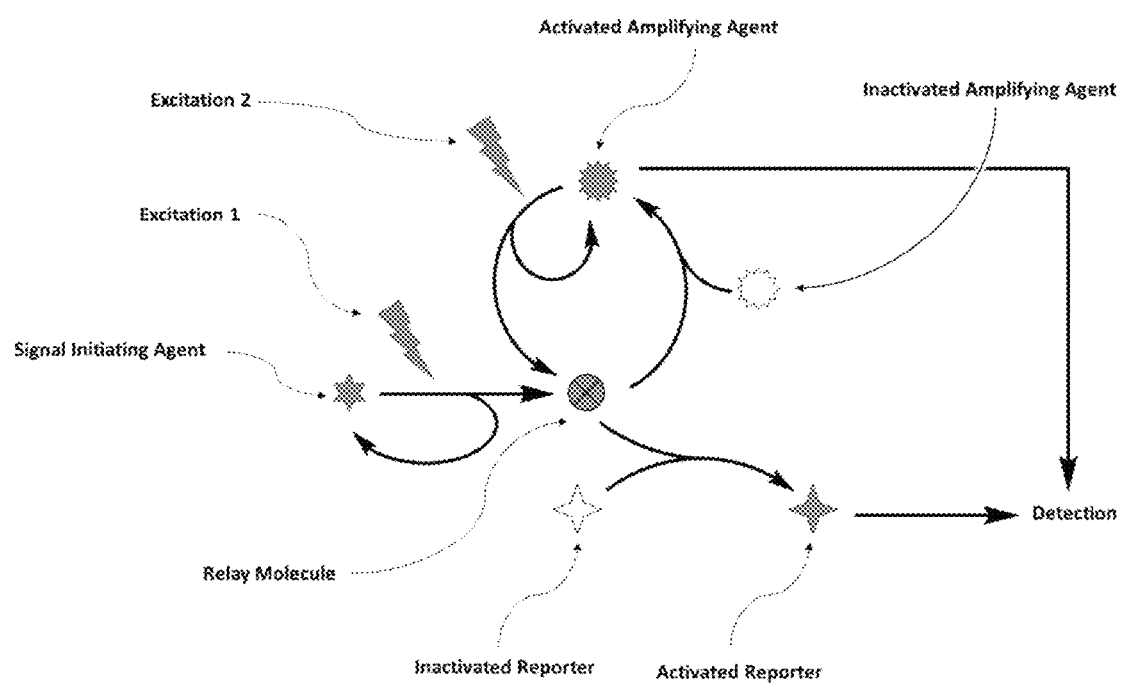
FIG. 21 depicts an illustration showing the self-accelerated and looped generation of the relay molecule by activated amplifying agent as initiated by the signal initiating agent, leading to the detection of signal from the activated amplifying agent and activated reporter.

In certain embodiments, the amplifying agent exhibits intrinsic fluorescence. In such embodiments, the fluorescence of the amplifying agent can optionally be detected; and step of determining based on the amplified reporting signal if the analyte is detected further comprises determining based on the detected fluorescence of the amplifying agent as illustrated in FIGS. 3 and 21. Detecting both the amplified reporting signal and the fluorescence of the amplifying agent can increase sensitivity of the method.

In instances in which the amplifying agent exhibits intrinsic fluorescence, the inactivated reporters/activated reporters can be omitted, and the fluorescence of the amplifying agent can be used to determine based on the detection of the intrinsic fluorescence of the amplifying agent if the analyte is detected in the sample. In such embodiments, the method can comprise:
  (a) providing a conjugate substrate complex, wherein the conjugate substrate complex comprises a substrate comprising a plurality of targeting moieties bound via an optional first linker to a surface of the substrate; and a plurality of conjugates, wherein each of the plurality of conjugates comprises a releasing moiety covalently bonded via an optional second linker to a signal initiating agent, wherein each of the releasing moieties is reversibly bound to at least one of the plurality of targeting moieties and each of the plurality of targeting moieties is capable of selectively binding the analyte;
  (b) providing a plurality of inactivated amplifying agents, wherein each inactivated amplifying agents comprises a masking group and an amplifying agent, and wherein the amplifying agent is fluorescent;
  (c) contacting the conjugate substrate complex and the sample, wherein in the presence of the analyte, one or more of the plurality of targeting moieties bind to the analyte causing the release of one or more of the plurality of conjugates from the conjugate substrate complex thereby forming one or more unbound conjugates;
  (d) exciting the one or more unbound conjugates with a first excitation means whereby excitation of the unbound conjugate induces the signal initiating agent to emit an initiating signal;
  (e) exposing a first inactivated amplifying agent to the initiating signal, whereby exposure of the first inactivated amplifying agent to the initiating signal induces at least one transformation selected from the group consisting of cleavage, chemical transformation, and electrical transformation of at least of one of the first inactivated amplifying agent or the masking group from the first inactivated amplifying agent thereby forming the first amplifying agent;

(f) exciting the first amplifying agent with a second excitation means whereby excitation of the first amplifying agent induces the first amplifying agent to emit a relay signal, wherein the relay signal optionally induces at least one transformation selected from the group consisting of cleavage, chemical transformation, and electrical transformation of at least one of another masked amplifying agent or the masking group of another masked amplifying agent;

(g) repeating step (f) one or more times thereby forming a plurality of amplifying agents;

(h) irradiating the plurality of amplifying agents with electromagnetic radiation thereby emitting an amplified reporting signal;

(i) detecting the amplified reporting signal using a detection means; and (j) determining based on the amplified reporting signal if the analyte is detected in the sample, wherein the first excitation means and the second excitation means are the same or different; and wherein the initiating signal and the relay signal are the same or different.

The first amplifying agent can be excited by exposure to a second excitation means whereby excitation of the first amplifying agent induces the first amplifying agent to emit a relay signal, wherein the relay signal optionally induces the release of the masking group of another masked amplifying agent.

The selection of the appropriate second excitation means can readily be accomplished by the skilled person. In certain embodiments, the selection of the appropriate second excitation means depends on the nature of the first amplifying agent. Exemplary seconds excitation means include, but are not limited to, a chemical reaction, such as but not limited to a chemical, electric current, heat, magnetic field, electromagnetic radiation, nuclear radiation, ultrasound, and any other form of energy. In certain embodiments, the first excitation means is electromagnetic radiation selected from the group consisting of gamma rays, X-rays, ultraviolet, visible, infrared, microwave, radio waves, and combinations thereof.

In certain embodiments, the second excitation means is visible light having a wavelength between 400-700 nm. In certain embodiments, the first excitation means is visible light between 400-650 nm, 450-650 nm, 450-600 nm, 450-550 nm, 475-525 nm, 500-525 nm, or 500-520 nm.

The step of exciting the first amplifying agent and emitting the relay signal can be repeated one or more times thereby forming a plurality of relay signals. In certain embodiments, the step of exciting the first amplifying agent and emitting the relay signal is repeated between $2\text{-}1\times10^{12}$; $2\text{-}1\times10^{11}$; $2\text{-}1\times10^{10}$; $10\text{-}1\times10^{10}$; $1\times10^{2}\text{-}1\times10^{10}$; $1\times10^{3}\text{-}1\times10^{10}$; or $1\times10^{4}\text{-}1\times10^{10}$. In certain embodiments, the step of exciting the first amplifying agent and emitting the relay signal is repeated more than 1, 5, 10, 100, 1,000, 10,000, 100,000, or 1,000,000 times.

Depending on the nature of the amplifying agent and the relay signal, each amplifying agent that is produced from the plurality of inactivated reporters can produce one or more relay signals.

The relay signal can be a small molecule, a radical, an oxidizing agent, a reducing agent, heat, light, or a combination thereof. In certain embodiments, the relay signal is singlet oxygen.

Exposing the plurality of inactivated reporters to the plurality of relay signals results in the formation of a plurality of activated reporters. The plurality of inactivated reporters can be any substance that upon exposure to the plurality of relay signals is converted into a substance that is capable of emitting an amplified reporting signal. Preferably, the plurality of inactivated reporters do not emit signals that are the same or substantially similar to the amplified reporting signal. Exposure of the plurality of inactivated reporters to the plurality of relay signals can result in a chemical, physical, and/or electrical transformation of the plurality of the plurality of inactivated reporters thereby forming the activated reporters.

In certain embodiments, the plurality of inactivated reporters have the formula:

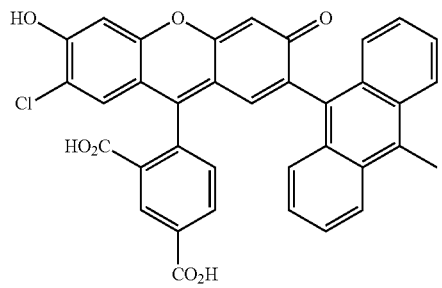 [SMILES: Cc1c2ccccc2c(-c2cc3c(-c4ccc(C(=O)O)cc4C(=O)O)c4cc(Cl)c(O)cc4oc-3cc2=O)c2ccccc12]

or a salt thereof.

In certain embodiments, the plurality of activated reporters have the formula:

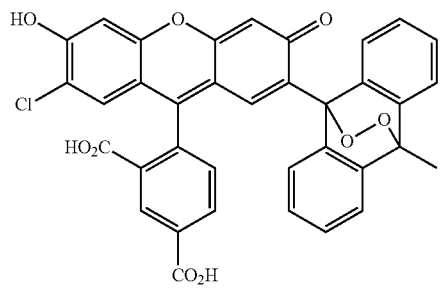 [SMILES: CC12OOC(c3cc4c(-c5ccc(C(=O)O)cc5C(=O)O)c5cc(Cl)c(O)cc5oc-4cc3=O)(c3ccccc31)c1ccccc12]

or a salt thereof.

Exciting the plurality of activated reporters generates an amplified reporting signal. In certain embodiments, the plurality of activated reporters are excited by a chemical, electric current, heat, magnetic field, electromagnetic radiation, nuclear radiation, ultrasound, and any other form of energy. In certain embodiments, the plurality of activated reporters are excited by gamma rays, X-rays, ultraviolet, visible, infrared, microwave, radio waves, or combinations thereof.

In certain embodiments, the plurality of activated reporters are excited using visible light having a wavelength between 400-700 nm. In certain embodiments, the plurality of activated reporters are excited using visible light having a wavelength between 400-700 nm. In certain embodiments, the 400-650 nm, 400-600 nm, 400-550 nm, 450-550 nm, 450-500 nm, 480-500 nm, or 480-490 nm.

The amplified reporting signal can be any detectable signal including, but not limited to, chemical, electric current, heat, magnetic field, electromagnetic radiation, nuclear radiation, ultrasound, and any other form of energy. In certain embodiments, the plurality of activated reporters are excited by gamma rays, X-rays, ultraviolet, visible, infrared, microwave, radio waves, or combinations thereof. In certain embodiments, the plurality of activated reporters are excited using visible light having a wavelength between 400-700 nm. In certain embodiments, the amplified reporting signal is luminescence having a wavelength between 400-700 nm. In certain embodiments, the 400-650 nm, 450-600 nm, 500-550 nm, 510-550 nm, 510-540 nm, or 520-530 nm.

Any detection means known to those skilled in the art can be used to detect the amplified reporting signal. In certain embodiments, the detection means is a calorimeter, a spectrometer, a NMR, a mass spectrometer, a gas chromatography system, a high pressure liquid chromatography (HPLC) system, a voltmeter, and combinations thereof.

In certain embodiments, the position of the releasing moiety and the targeting moiety in the conjugate substrate complex can be exchanged. FIG. 1B illustrates the structure of such embodiments of the conjugate substrate complex and the formation of the unbound conjugate in accordance with certain embodiments described herein. In reference to FIG. 1B, the conjugate substrate complex (100) comprising a plurality of releasing moieties (104) each releasing moiety (104) bound to the substrate (101) via an optional first linker (102); and a plurality of conjugates (108), each conjugate (108) comprising the targeting moiety (103), bound via an optional second linker (105) to the signal initiating moiety (106). In the presence of the analyte (200), one or more of the plurality of conjugates (108) can be displaced when the analyte (200) binds to one or more of the plurality of targeting moieties (103) thereby forming the unbound conjugate (301).

In instances in which the methods described herein utilize the conjugate substrate complex illustrated in FIG. 1B, the method for detecting an analyte in a sample suspected of containing the analyte can comprise:

(a) providing a conjugate substrate complex, wherein the conjugate substrate complex comprises a substrate comprising a plurality of releasing moieties bound via an optional first linker to a surface of the substrate; and a plurality of conjugates, wherein each of the plurality of conjugates comprises a targeting moiety covalently bonded via an optional second linker to a signal initiating agent, wherein each of the targeting moieties is reversibly bound to at least one of the plurality of releasing moieties and each of the plurality of targeting moieties is capable of selectively binding the analyte;

(b) providing a plurality of inactivated amplifying agents, wherein each inactivated amplifying agents comprises a masking group and an amplifying agent;

(c) providing a plurality of inactivated reporters;

(d) contacting the conjugate substrate complex and the sample, wherein in the presence of the analyte, one or more of the of targeting moieties bind to the analyte causing the release of one or more of the plurality of conjugates from the conjugate substrate complex thereby forming one or more unbound conjugates;

(e) exciting the one or more unbound conjugates with a first excitation means whereby excitation of each of the one or more unbound the conjugate induces the signal initiating agent to emit an initiating signal;

(f) exposing a first inactivated amplifying agent to the initiating signal, whereby exposure of the first inactivated amplifying agent to the initiating signal induces at least one transformation selected from the group consisting of cleavage, chemical transformation, and electrical transformation of at least one of the first inactivated amplifying agent or the masking group from the first inactivated amplifying agent thereby forming the first amplifying agent;

(g) exciting the first amplifying agent with a second excitation means whereby excitation of the first amplifying agent induces the first amplifying agent to emit a relay signal, wherein the relay signal optionally induces at least one transformation selected from the group consisting of cleavage, chemical transformation, and electrical transformation of at least one of another inactivated amplifying agent or the masking group of another masked amplifying agent;

(h) repeating step (g) one or more times thereby forming a plurality of relay signals;

(i) exposing the plurality of inactivated reporters to the plurality of relay signals whereby exposure of the plurality inactivated reporters to the plurality of relay signals forms a plurality of activated reporters;

(j) exciting the plurality of activated reporters thereby emitting an amplified reporting signal;

(k) detecting the amplified reporting signal using a detection means; and (l) determining based on the amplified reporting signal if the analyte is detected in the sample, wherein the first excitation means and the second excitation means are the same or different; wherein the initiating signal and the relay signal are the same or different; and wherein the releasing moiety, the substrate, the optional first linker; the targeting moiety; the optional second linker; the signal initiating moiety; the first amplifying agent; the inactivated reporter; the initiating signal; the first excitation means; the second excitation means; the relay signal; the amplified reporting signal; the detection means are each independently as described in any embodiment or combination of embodiments disclosed herein.

In certain embodiments, each of the plurality of conjugates is selected from the group consisting of:

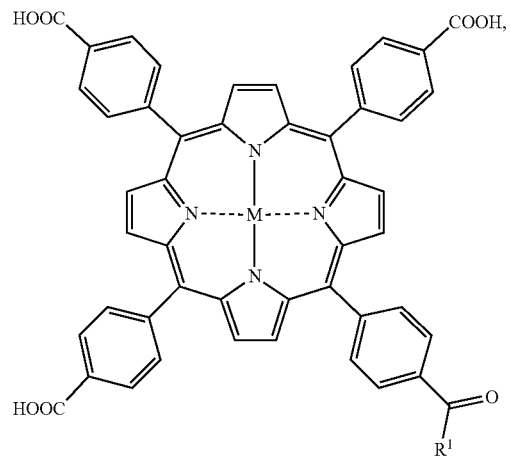

33
-continued

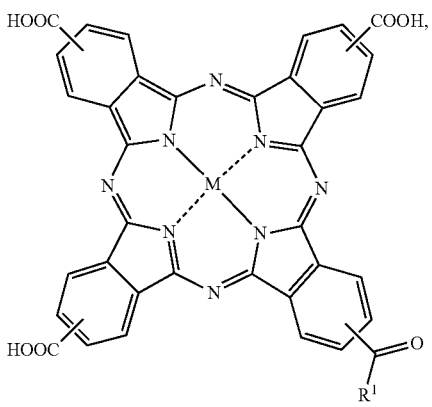

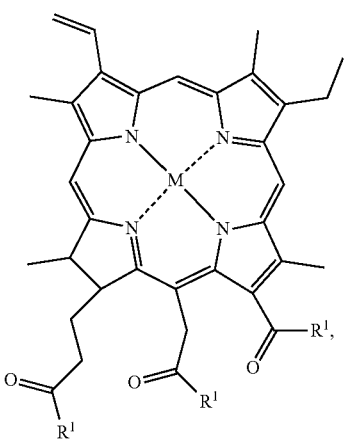

34
-continued

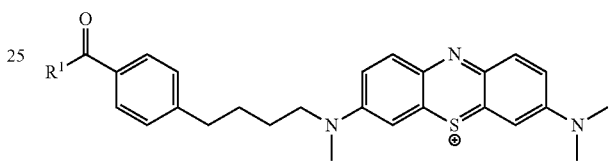

or a salt thereof, wherein $R^1$ is —X—$Y^1$ or OH, wherein X is the linker, M is 2H or a non-paramagnetic metal, and $Y^1$ is the targeting moiety, with the proviso that only one $R^1$ is —X—$Y^1$.

In certain embodiments, each of the plurality of conjugates has the formula:

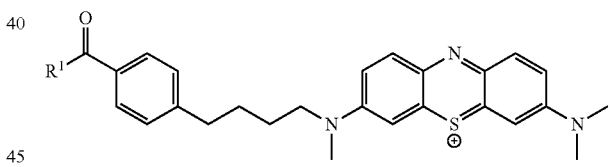

or a salt thereof, wherein $R^1$ is —X—$Y^1$ or OH, wherein X is the linker and $Y^1$ is the targeting moiety.

In certain embodiments, each of the plurality of conjugates has the formula:

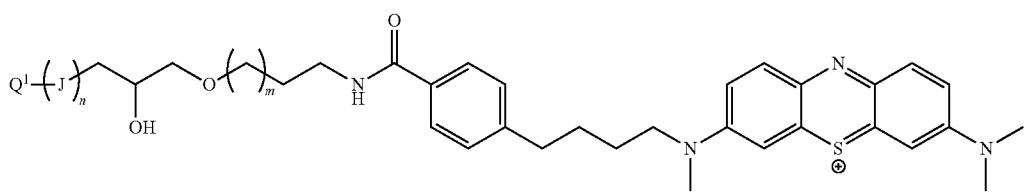

or a conjugate salt thereof, wherein m is a whole number selected from 0-2, n is a whole number selected from 3-5; J for each instance is a nucleotide independently selected from the group consisting of A, C, G, and T; and $Q^1$ is the targeting moiety.

The methods described herein can be conducted in aqueous solution. In certain embodiments, the methods described are conducted in phosphate-buffered saline.

In certain embodiments, the method is conducted at a temperature between 0° C.-200° C.; 0° C.-150° C.; 0° C.-100° C.; 0° C.-50° C.; 20° C.-50° C.; or 20° C.-30° C.

The methods provided herein enable accurate detection of extremely low abundance analytes. In certain embodiments, the limit of detection (LOD) of the method is 0.1-100 fmol, 0.1-10 fmol, 0.1-1 fmol, 0.1-0.5 fmol, 0.2-0.5 fmol, 0.3-0.5 fmol, or 0.3-0.4 fmol. In certain embodiments, the limit of quantification (LOQ) of the method is 0.01-100 fmol, 0.01-10 fmol, 0.01-1 fmol, 0.01-0.1 fmol, 0.01-0.5 fmol, 0.01-0.1 fmol, 0.01-0.05 fmol, or 0.01-0.04 fmol.

EXAMPLES

Autocatalytic Relay Loop for DNA Detection

The analyte detection mechanism described herein calls for the presence of the probe-conjugate to initiate the autocatalytic cycles. In the presence of the probe-conjugate with proper excitation, the probe-conjugate generates an initiating signal. The initiating signal can be any form of energy or molecules which can further activate the inactivated amplifying agent into the activated amplifying agent.

Referring to FIG. 3, in the case DNA detection, in certain embodiments, the probe-conjugate can comprise a releasing moiety comprising DNA and a signaling agent comprising a photosensitizer (DNA-photosensitizer conjugate). The excitation of photosensitizer can convert oxygen to ROS such as singlet oxygen, radicals, or other oxidizing agents as the initiating signal. The photosensitizer can be excited by optimized wavelength or ultrasound. The amount of input energy can govern the amount of ROS generation. The ROS can further dequench the inactivated amplifying agent to the amplifying agent, which is also a photosensitizer that can also generate ROS.

After a series loops of autocatalyzed reaction, a high concentration of ROS can be generated by both the DNA-photosensitizer conjugates and the amplifying agent. The inactivated reporter can be added into the system after performing the loops of autocatalyzed reaction or added together with inactivated amplifying agent. Lastly, through proper excitation of the activated reporter, an amplified fluorescent signal can be generated and thus, able to be detected by a detector.

Figure 4:
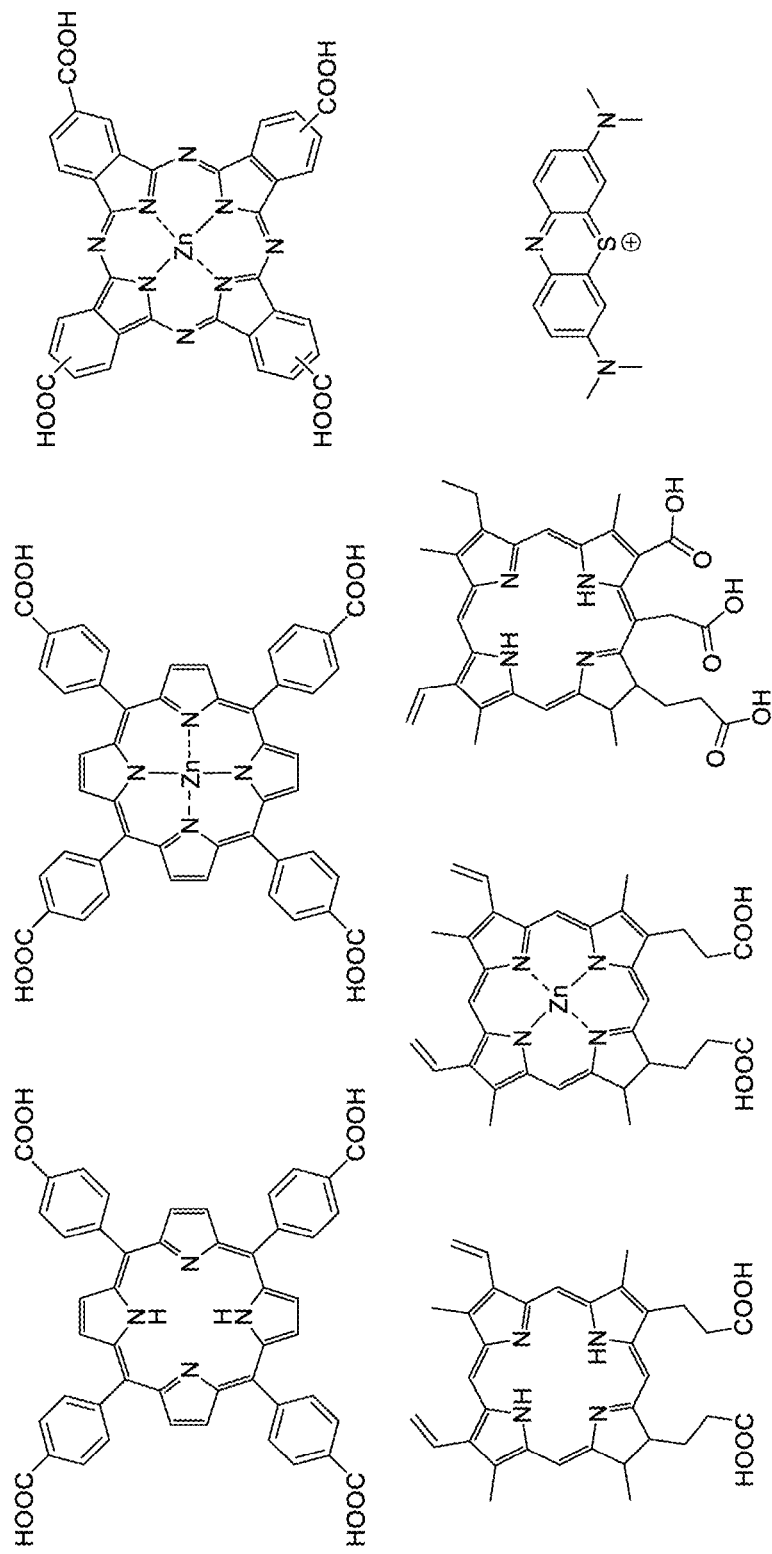
FIG. 4 depicts some examples of the commercially available photosensitizers that were screened in certain embodiments of the methods described herein.

To design the DNA-photosensitizer conjugate, a photosensitizer with specific functional groups were investigated, including porphyrin derivatives, protoporphyrin derivatives, chlorin e6, phthalocyanine derivatives, and MB derivatives (FIG. 4). Among many photosensitizers, the best choice of photosensitizers should preferably be water soluble and compatible with biomolecules. After screening different photosensitizers, MB showed to work best in our novel reaction with acceptable solubility and radical generation efficiency. Any bioconjugation reactions, amide bond or ester bond coupling can be used to form the conjugates. The products of the conjugation reaction were analysed and purified by agarose gel electrophoresis.

Figure 5:
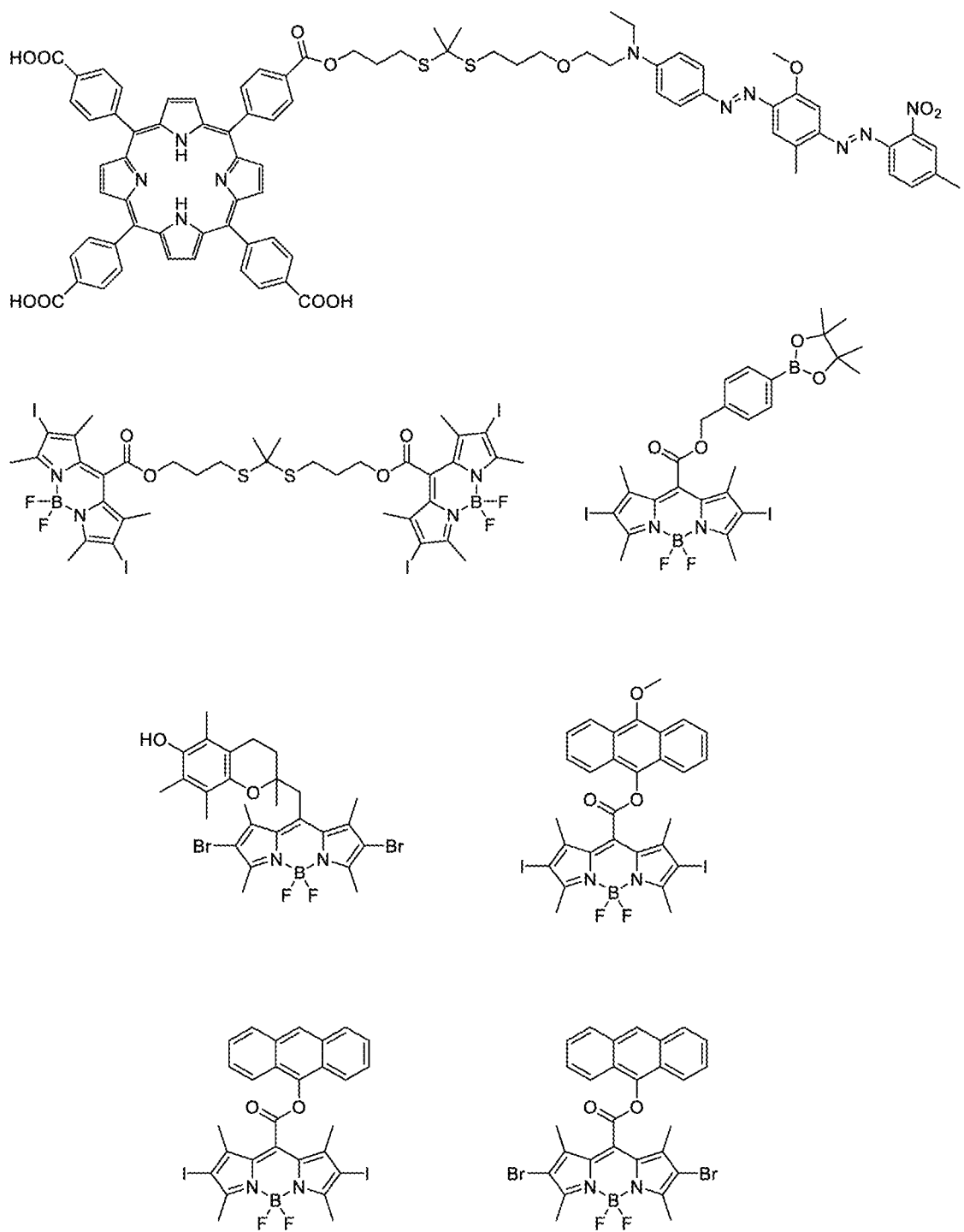
FIG. 5 depicts exemplary amplifying agents according to certain embodiments described herein.

For the inactivated amplifying agent, it can comprise a photosensitizer that contains one or more functional/masking groups that can quench the photodynamic activity of the photosensitizer and can be restore the photodynamic activity by reacting with ROS to form or release the activated amplifying agent. The activated amplifying agent can be a photosensitizer that can be excited again to generate the relay signals, e.g., ROS. Numerous designs of the inactivated amplifying agent were proposed and some of them were synthesized to test the amplifying efficiency (FIG. 5). The activation strategies were mainly by detaching the quenching moiety thought ROS-cleavable linkers, or by reacting with the ROS-responsive quencher itself.

The inactivated reporter can be any molecules that can be quenched by a functional/masking group. In the presence of relay signals, the inactivated reporter can be dequenched to form an activated reporter. In the examples herein, a commercially available fluorogenic probe was used for ROS-detection called Singlet Oxygen Sensor Green (SOSG). This molecule can generate fluorescence in the presence of ROS. The fluorescent signal intensity is proportional to the amount of ROS in the system for quantitative analysis.

General

All the reactions were performed under an atmosphere of nitrogen. All solvents and reagents were of ACS or reagent grade and used as received. All the reactions were monitored by thin layer chromatography (TLC) on Merck Millipore pre-coated silica gel 60 F254. Chromatographic purification was performed on Macherey-Nagel silica gel with the indicated eluents. Mass spectra of the DNAs were obtained with an Agilent 6540 ESI-QTOF UPLC system with an ACQUITY UPLC HSS T3 column using 10 mM ammonium acetate in acetonitrile or Milli-Q water as the gradient eluent. Mass spectra of DNAs were analyzed by Agilent MassHunter Qualitative Analysis software version B.06.00. The concentration of the stock solution of DNA was determined by the absorption of the DNA at 260 nm using a Nanodrop 2000c spectrometer. Fluorescence measurement was done on a Thermo Varioskan Flash Multimode Microplate Reader. Nuclear magnetic resonance (NMR) spectroscopy was performed on a Bruker Advance-III 400 MHz FT-NMR System. The UV-Vis spectra were obtained by a Cary 3500 UV-Vis Spectrophotometer.

Example 1—Synthesis of Iron Oxide Particle-DNA/DNA-MB Complex

The disease-related DNAs ranging from 12 to 60 base-pair was conjugated to a N-hydroxysuccinimide (NHS)-modified MB. A DNA with complementary sequence would be conjugated onto IOP for hybridizing the DNA-MB conjugate. The oligonucleotides were purchased from Integrated DNA Technologies, Inc. and IOP with NHS preinstalled on the surface was purchased at Micromod Partikeltechnologie GmbH. A tumor-activating mRNA sequence was used in the demonstration of the technique. A short spacer of non-binding sequence composed of 5 adenine units was added as spacer between conjugation sites and functional part of the DNAs to reduce the steric interference. An amine linker was added to the 3' end of the DNA sequences that can conjugate to other moieties, for example, releasing DNA sequence for conjugating photosensitizer CCTCAACGTTAG, 5'-3' (SEQ ID NO: 4); targeting DNA sequence for attaching on solid supports TTGGTGAAGCTAACGTTGAGG, 5'-3' (SEQ ID NO: 3) as depicted with additional five adenosine nucleotide spaces in $DNA_R$ (SEQ ID NO: 1) and $DNA_T$ (SEQ ID NO: 2) shown in FIG. 2.

Figure 6:
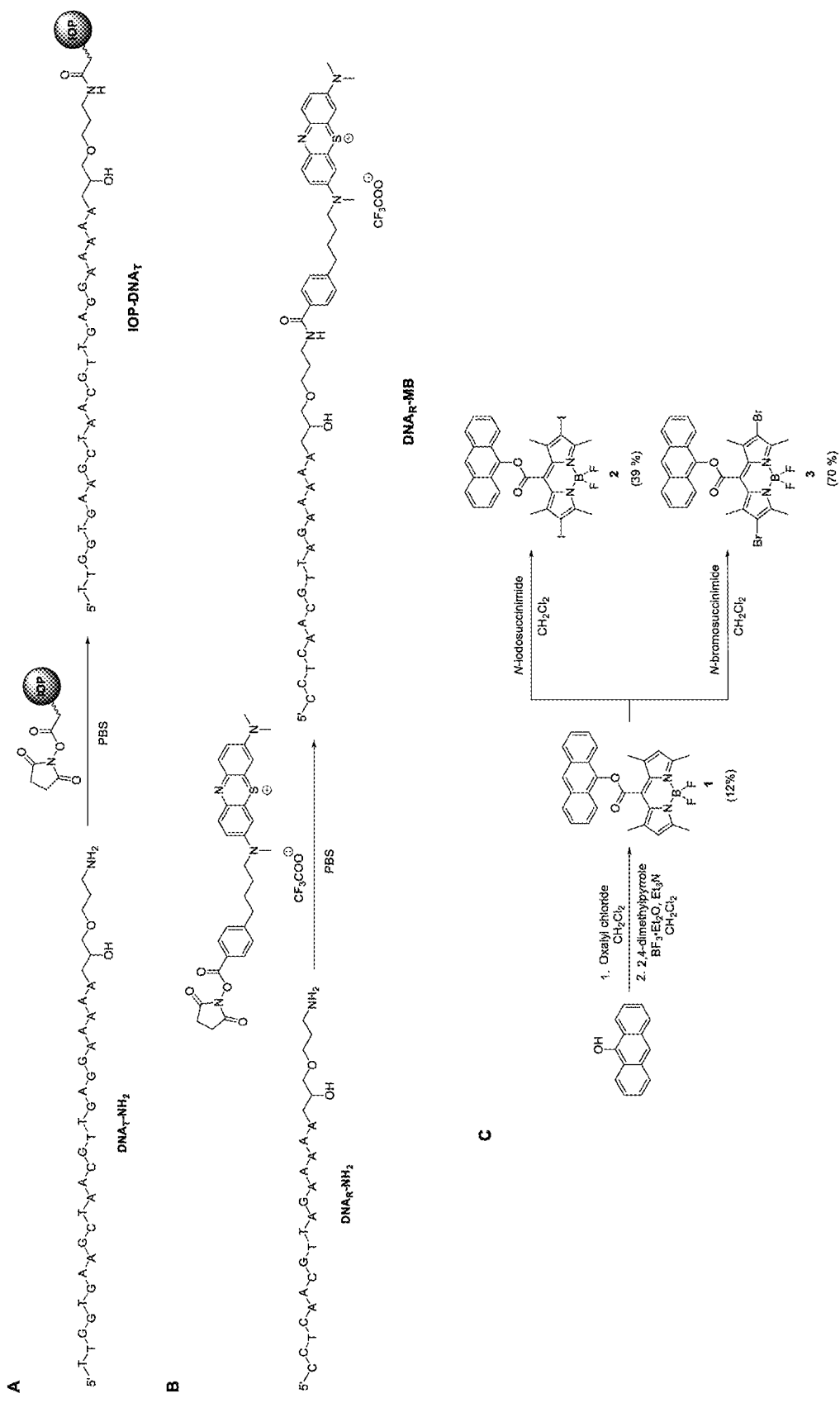
FIG. 6 depicts exemplary synthetic routes of IOP-$DNA_T$ (SEQ ID NO: 2), $DNA_R$-MB (SEQ ID NO: 1), and compounds 2 and 3.
Figure 7:
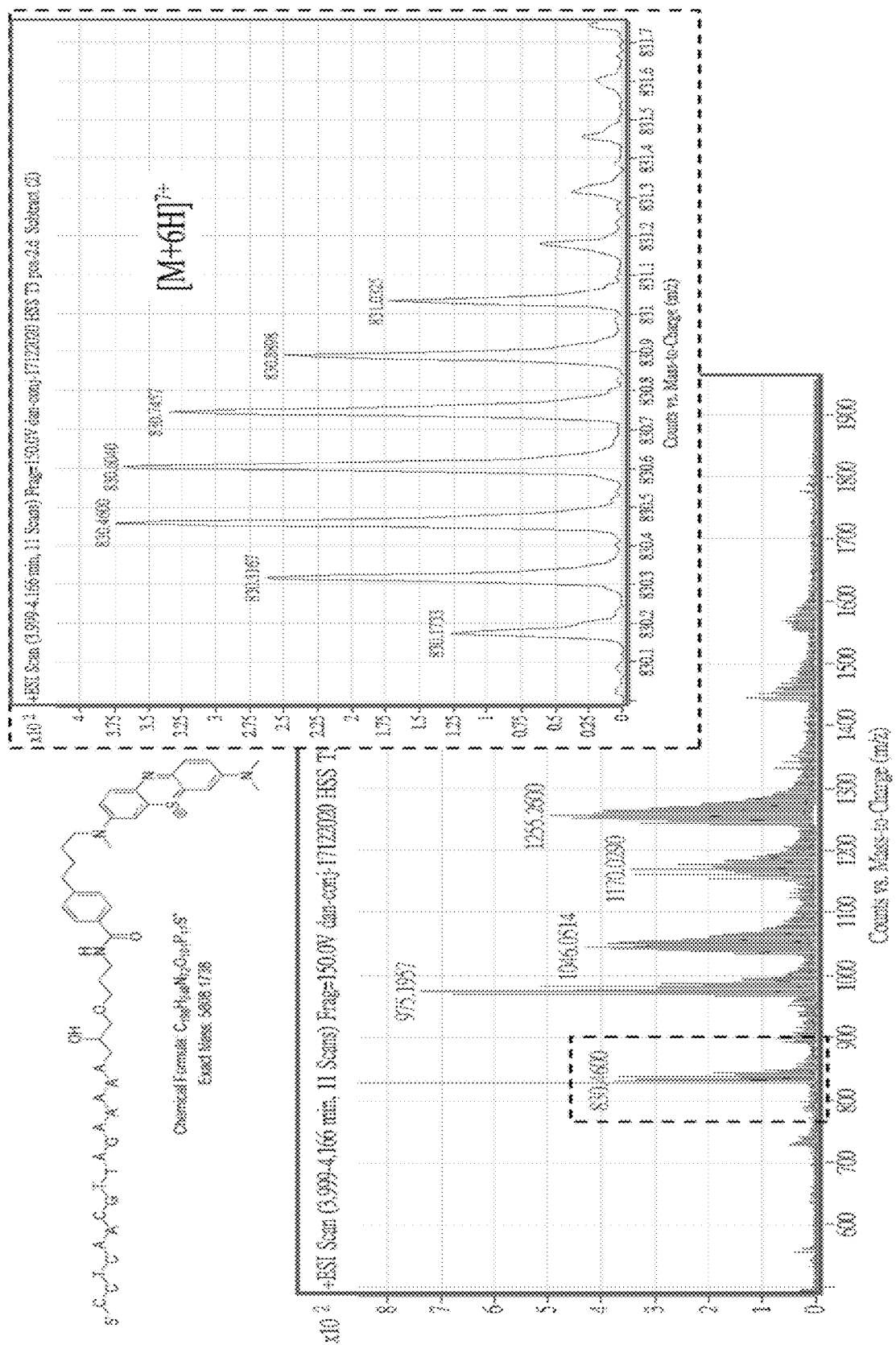
FIG. 7 depicts isotopic clusters of the multi-charged $DNA_R$ (SEQ ID NO: 1)-MB conjugate obtained by an ESI-QTOF mass spectrometer.

$DNA_R$ (200 µM, 10 µL) and the NHS-modified MB (7 mM, 1 µL) were mixed in 40 µL pH 7.4 PBS and was shaken at room temperature for 4 h (FIG. 6B). The presence of $DNA_R$-MB conjugate was characterized by UPLC-high-resolution mass spectrometry using 10 mM ammonium acetate in acetonitrile and 10 mM ammonium acetate in water as gradient eluents (FIG. 7). The crude mixture was used without further purification.

Figure 8:
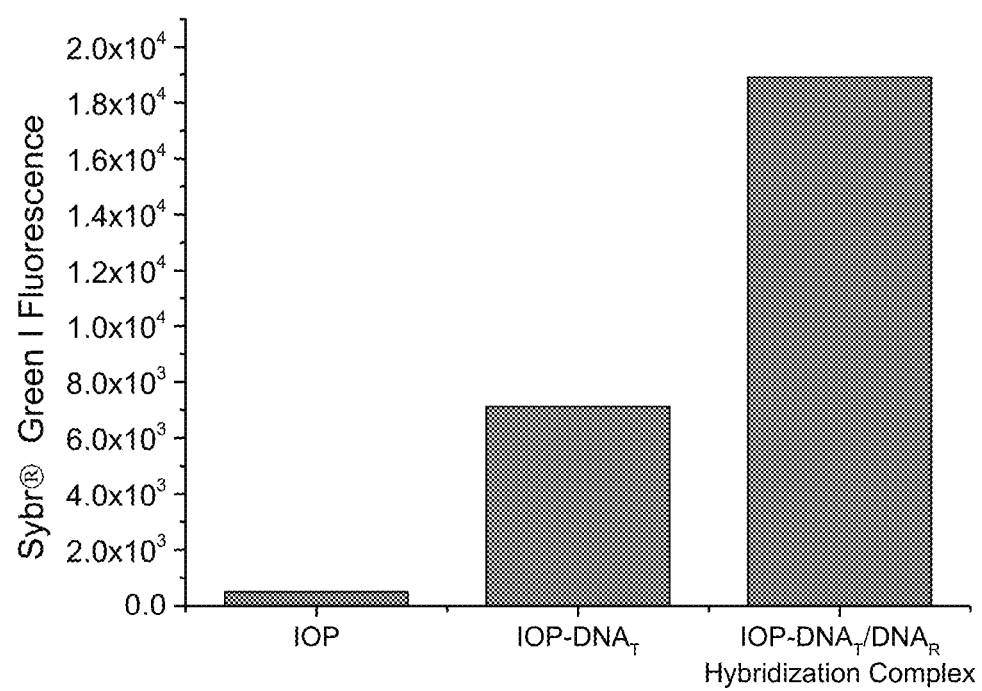
FIG. 8 depicts the comparison of the fluorescence intensities of SYBR Green before and after DNA conjugation and hybridization on IOP.

The IOP (50 mg) was first dispersed in 50 μL pH 7.4 PBS for 30 s. The $DNA_T$ (40 μM, 400 μL) was added to the IOP and the mixture was shaken for 16 h (FIG. 6A). The mixture was then washed with PBS for 5 times. The IOP was then dispersed in 800 μL pH 7.4 Tris-EDTA (TE) buffer for storage. Final concentration of the IOP solution was 5.88 wt %. The successful conjugation of $DNA_T$ to IOP was confirmed by the presence of Sybr® Green I fluorescence after binding to the $DNA_T$ on the surface of the IOP. 50 μL of the IOP solution was centrifuged and the supernatant was replaced with 1× Sybr® Green I stain in TE buffer. The solution was shaken for 15 min and the IOP was washed with TE buffer 3 times. The solution was then transferred to a 385-well plate and the Sybr® Green I fluorescence emission was measured at 535 nm with excitation at 495 nm (FIG. 8).

Figure 9:
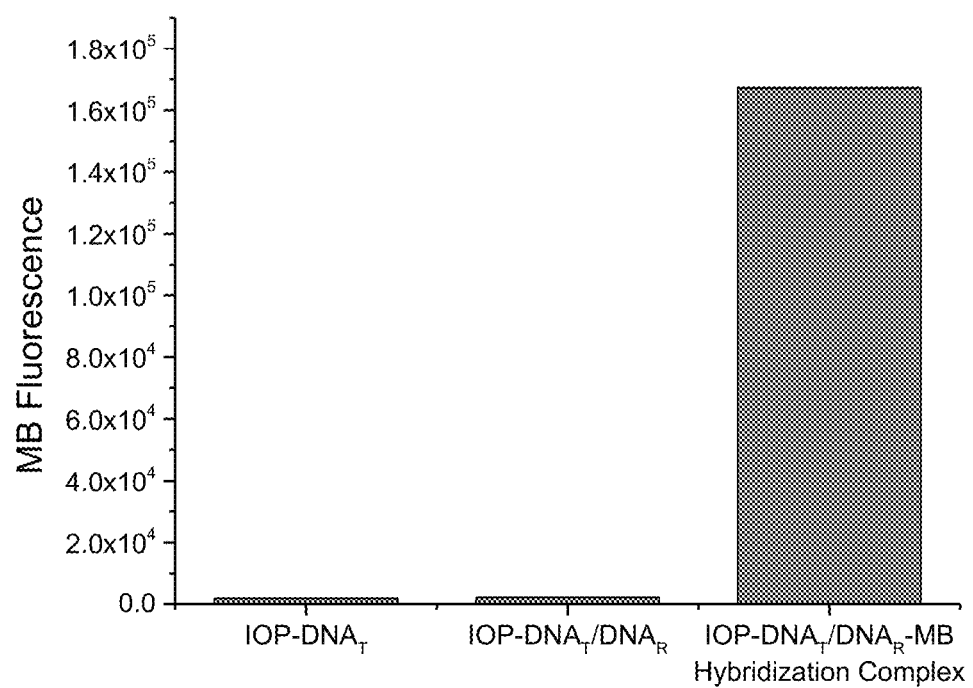
FIG. 9 depicts the comparison of the fluorescence intensities of MB before and after DNA hybridization on TOP.

To prepare the IOP/MB hybridization complex, the $DNA_R$-MB (40 μM, 40 μL) and IOP-$DNA_T$ (6 mg, 102 μL) were mixed with 60 μL PBS and shaken for 30 min to allow hybridization. The complex was then washed 5 times and stored with 200 μL pH 7.4 TE buffer with 0.05% Tween80. Final concentration of the IOP solution was 2.91 wt %. The successful hybridization of $DNA_R$-MB to IOP-$DNA_T$ was confirmed by the presence of the strong MB fluorescence from the washed particle. 50 μL of the IOP/MB complex solution was transferred to a 385-well plate and the MB fluorescence emission was measured at 690 nm with excitation at 640 nm (FIG. 9).

Example 2—Synthesis of Inactivated Amplifying Agent 2 and 3

The synthesis of compounds 1, 2, and 3 is shown in FIG. 6C.

9-Hydroxyanthracene (200 mg, 1.0 mmol) was first dissolved in dry dichloromethane ($CH_2Cl_2$). Oxalyl chloride (600 μL, 3.7 mmol) was added to the solution and stirred overnight. The volatiles were then removed in vacuum at 70° C. The residue was then redissolved in $CH_2Cl_2$ and 2,4-dimethylpyrrole (800 μL, 7.8 mmol) was added and the solution was stirred for 1 hour at room temperature. After that, boron trifluoride-ether complex (2.0 mL, 16 mmol) was added to the above mixture, followed by dropwise addition of triethylamine (1.0 mL, 7.2 mmol). After stirring for 3 h at room temperature, the solvent was removed under reduced pressure. The residue was purified by silica chromatography using n-hexane:ethyl acetate (EA) 4:1 (v:v) as eluent. Compound 1 afforded a red solid (30 mg, 12%).

To synthesize inactivated amplifying agent 2, 1 (10 mg, 21 μmol) was dissolved in $CH_2Cl_2$ and N-iodosuccinimide (11 mg, 49 μmol) was added in dark. The solution was stirred for 1 hour and the solvent was removed under reduced pressure. The residue was purified by silica chromatography using EA:n-hexane 1:4 (v:v) as eluent. Compound 2 afforded as a reddish purple solid (6 mg, 39%).

To synthesize inactivated amplifying agent 3, 1 (10 mg, 21 μmol) was dissolved in $CH_2Cl_2$ and N-bromosuccinimide (8 mg, 45 μmol) was added in dark. The solution was stirred for 1 hour and the solvent was removed under reduced pressure. The residue was purified by silica chromatography using EA:n-hexane 1:4 (v:v) as eluent. Compound 3 afforded as a reddish purple solid (9 mg, 67%).

Figure 10:
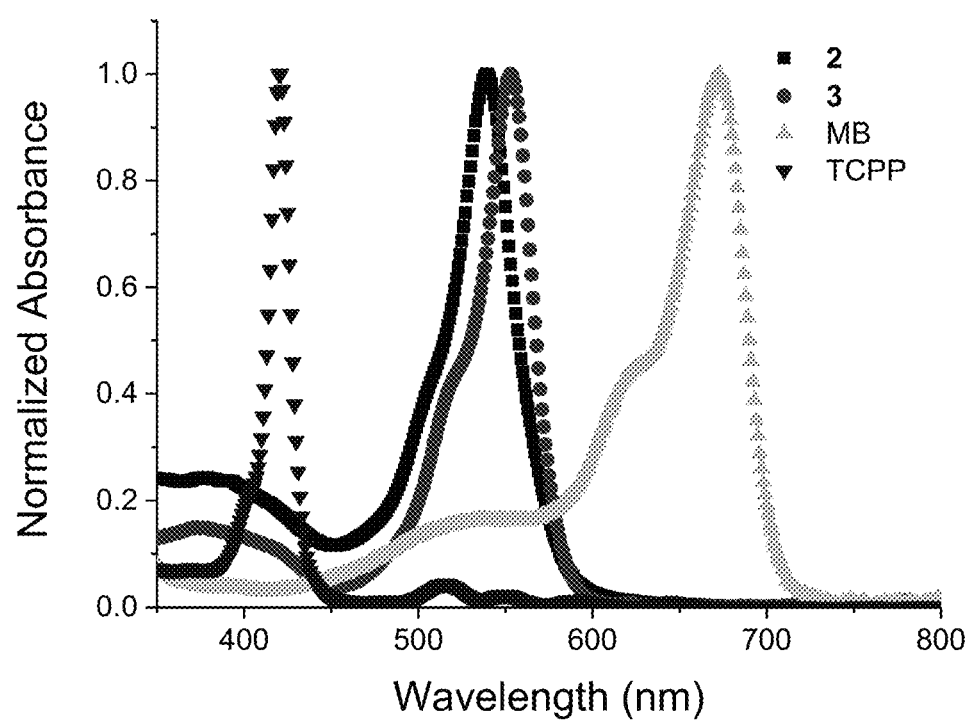
FIG. 10 depicts the normalized absorption spectra of TCPP, MB, inactivated amplifying agents 2, and 3.
Figure 11:
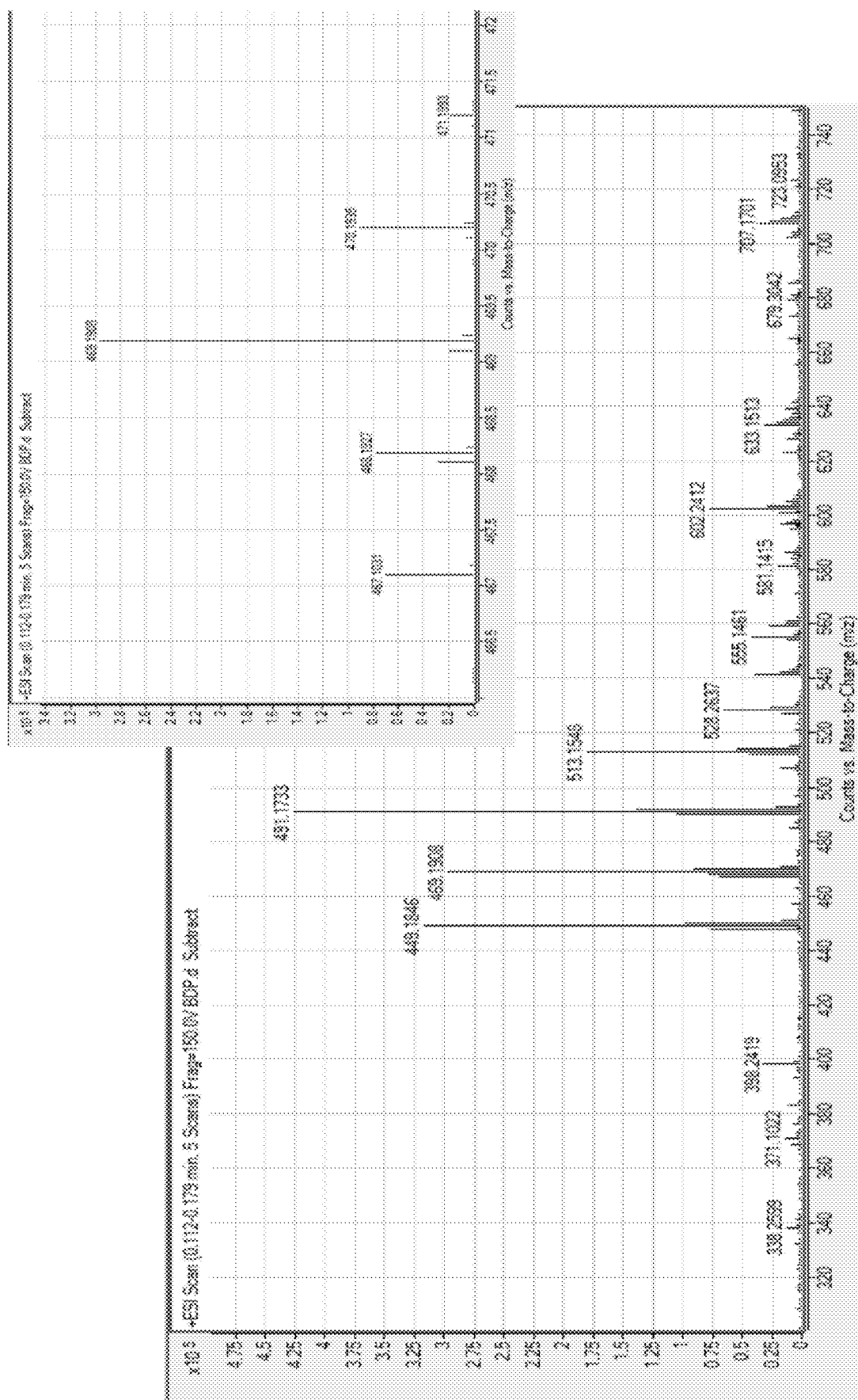
FIG. 11 depicts the high-resolution mass spectrum of compound 1 obtained by a ESI-QTOF mass spectrometer.
Figure 12:
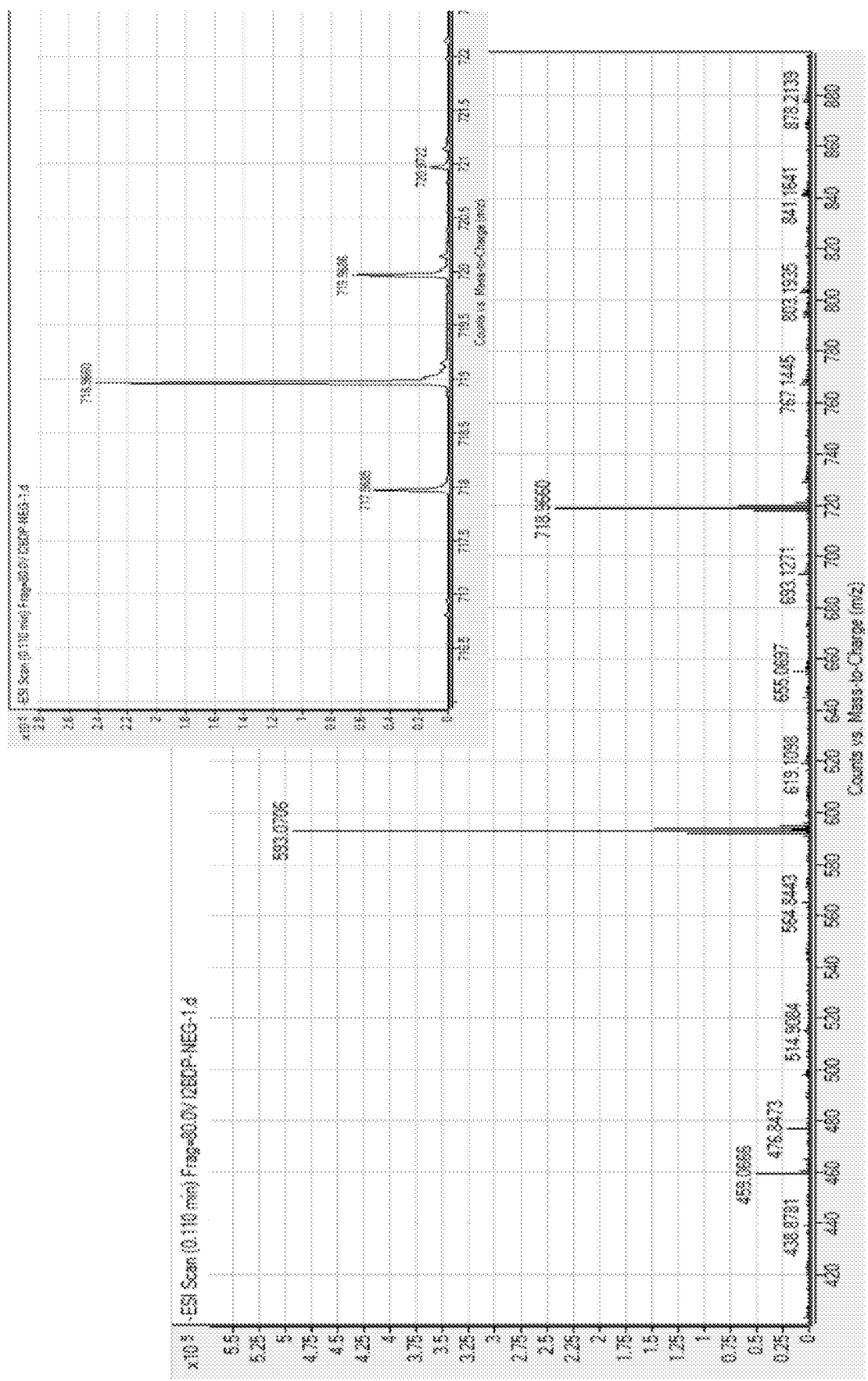
FIG. 12 depicts the high-resolution mass spectrum of compound 2 obtained by a ESI-QTOF mass spectrometer.
Figure 13:
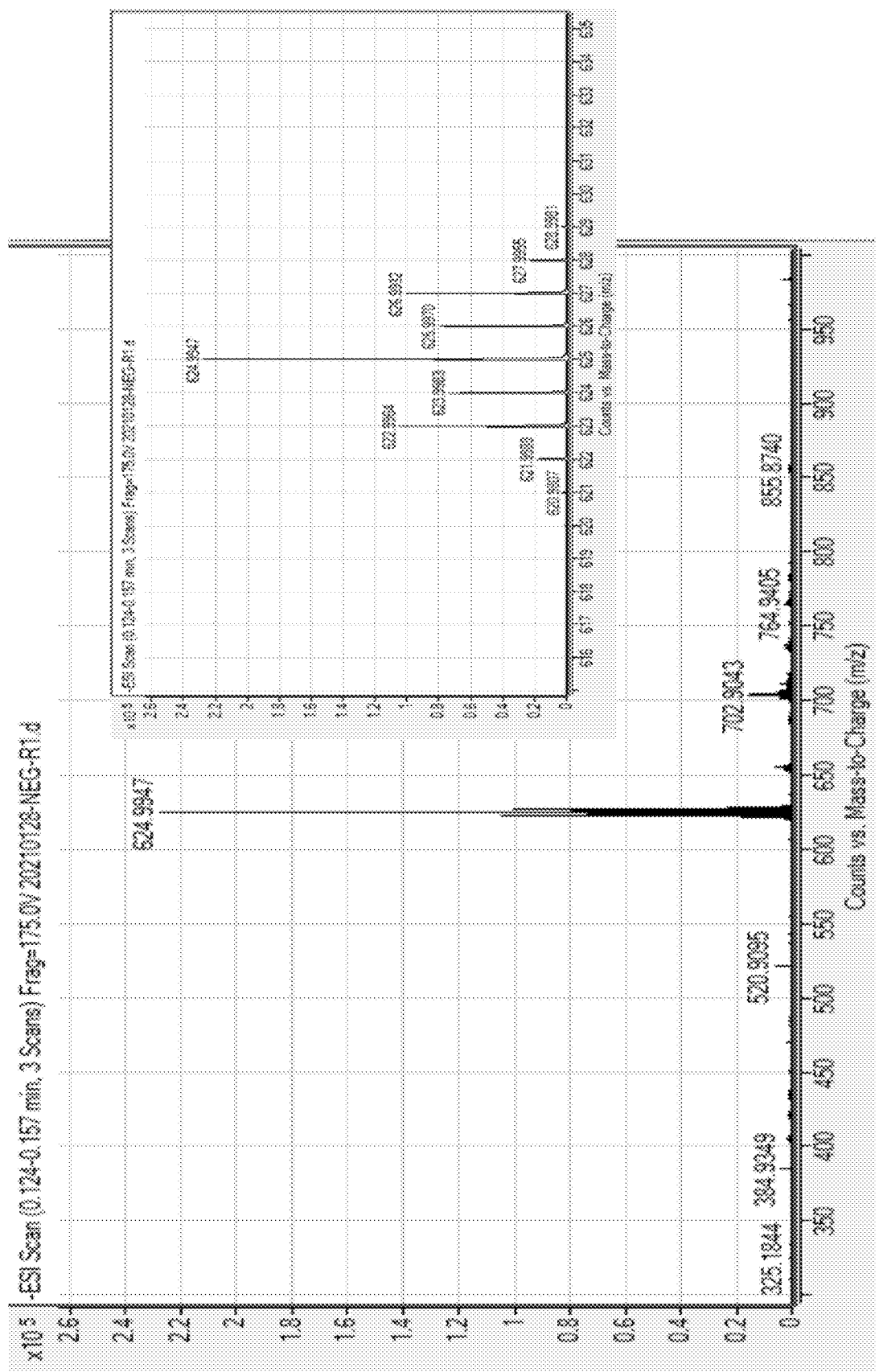
FIG. 13 depicts the high-resolution mass spectrum of compound 3 obtained by a ESI-QTOF mass spectrometer.

All the compounds were characterized by UV-Vis absorption (FIG. 10) and NMR spectroscopies and high-resolution mass spectrometry (FIGS. 11-13).

Figure 14:
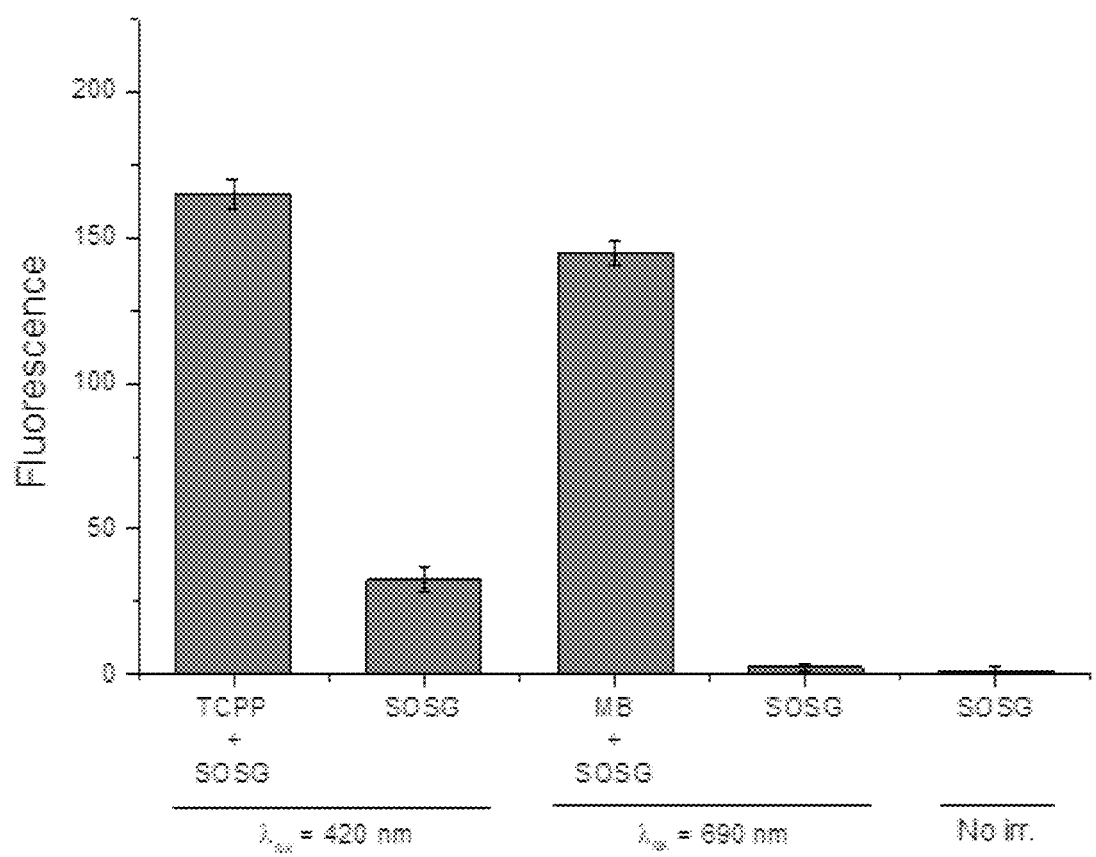
FIG. 14 depicts the comparison of the fluorescence intensities of SOSG induced by the irradiation of different wavelengths of light in the presence or absence of TCPP or MB.
Figure 15:
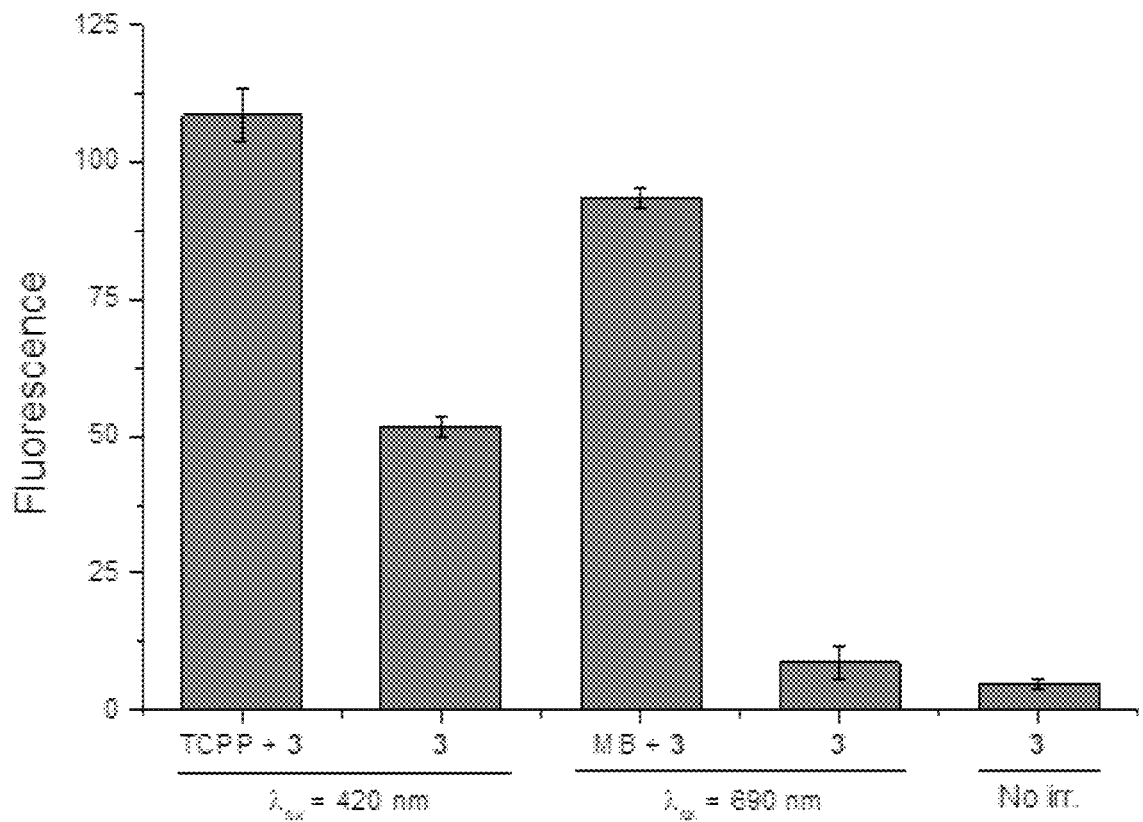
FIG. 15 depicts the comparison of the fluorescence intensities of inactivated amplifying agent 3 induced by the irradiation of different wavelengths of light in the presence or absence of TCPP or MB.

Example 3—Matching the Suitable Signal Initiating Photosensitizer for the Inactivated Amplifying Agent and the Inactivated Reporter To minimize the unwanted activation of the inactivated amplifying agents or reporters by direct light irradiation rather than single oxygen, the irradiation wavelength should avoid the absorption of those molecules. As the irradiation wavelength is determined by the photosensitizers that are used in the loop amplification, photosensitizers with distinct excitation wavelengths were tested. Tetrakis(4-carboxyphenyl)porphyrin (TCPP) and MB are two common photosensitizers that absorption at around 400-450 nm and 600-700 nm respectively (FIG. 10). 10 μM inactivated amplifying agent 3 and inactivated reporter SOSG were mixed and irradiated at 10 W of their respective wavelengths for 3 min with and without 0.1 μM photosensitizers. FIGS. 14 and 15 show the effect of light with different wavelengths to inactivated amplifying agent 3 and SOSG. Both photosensitizers can efficiently activate 3 and SOSG with their respective wavelengths by generating singlet oxygen. However, while the light of 420 nm activated 3 and SOSG significantly even without the presence of TCPP, the light of 690 nm barely had any effect on the two probes. These shows using MB with 690 nm as irradiation wavelength can minimize the unwanted activation of the probes.

Example 4—Demonstrating the Singlet-Oxygen-Responsive ROS Generation Ability of Inactivated Amplifying Agent 2 and 3

Figure 16:
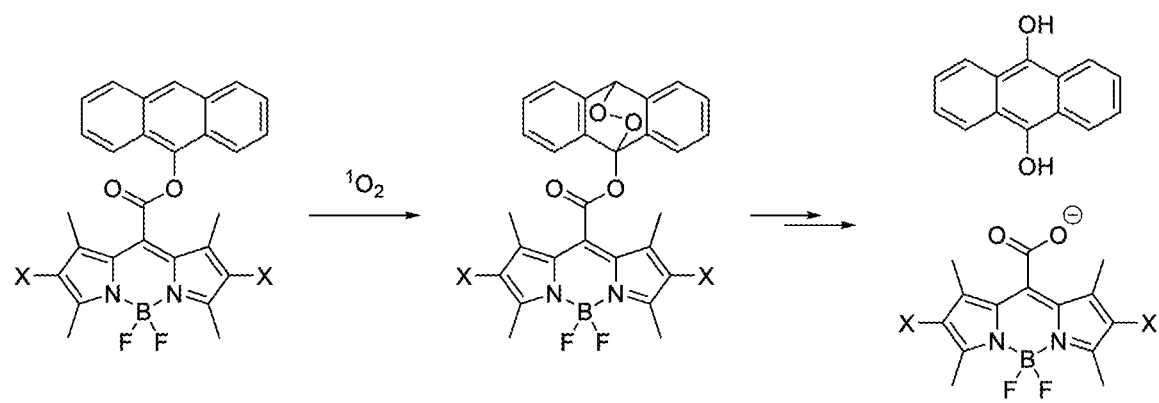
FIG. 16 depicts the cleavage mechanism of inactivated amplifying agent 2 and 3 by singlet oxygen.
Figure 17:
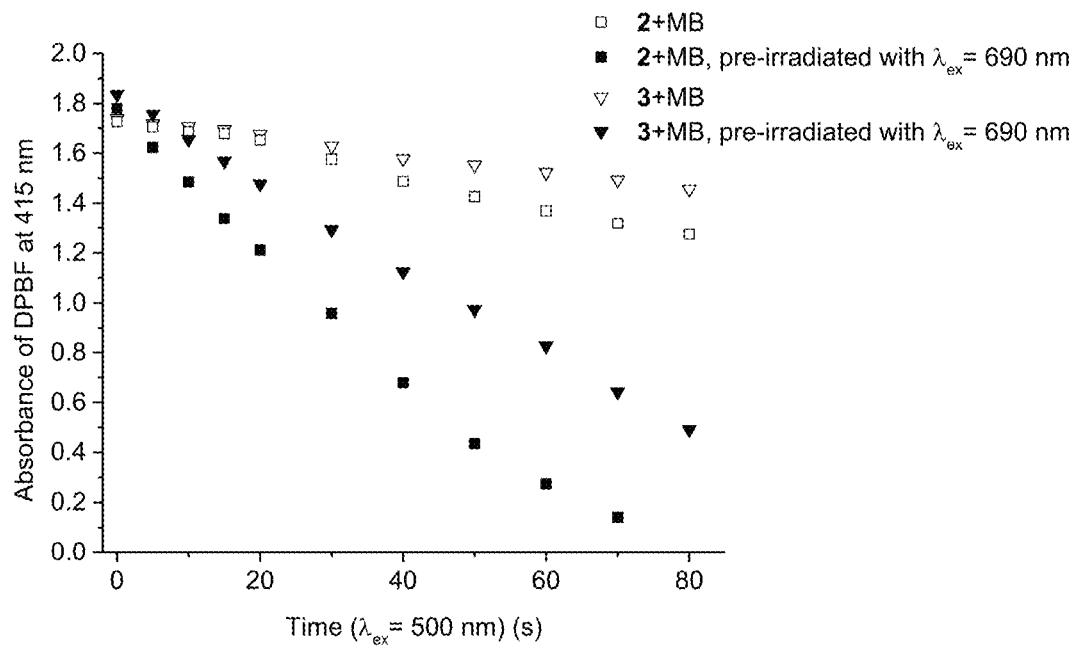
FIG. 17 depicts the absorbance decay of DPBF as sensitized by inactivated amplifying agents 2 and 3 under the irradiation of 500 nm with or without pre-irradiation of the light of 690 nm.

Inactivated amplifying agent 2 and 3 can react with singlet oxygen and lead to the cleavage of the anthracene quencher to restore the ROS generation ability (FIG. 16). To study their singlet-oxygen-responsive properties, 1,3-diphenylisobenzofuran (DPBF) was used as a scavenger for the singlet oxygen generated in the solution. The abundance of the radical would be reflected by the decrease of the absorbance of DPBF. 3 mL of 2 or 3 (1 μM) were first irradiated by light of 690 nm with or without the presence of 1 μM MB for 5 min. 10 μL DPBF (9 mM) was then added to the solution and irradiated with light of 500 nm. The absorbance of DPBF at 415 nm was recorded and shows in FIG. 17. With the pre-activation of 2 and 3 by singlet oxygen generated by MB, the activated products generated significantly more singlet oxygen than those without pre-activation, as shown by the decrease in the absorbance of DPBF while the irradiation proceeded. This suggests the singlet oxygen generation abilities of 2 and 3 were dequenched by the singlet oxygen generated at the pre-irradiation stage.

Example 5—Performing the Autocatalytic Relay Loop Amplification Using IOP/MB Complex as DNA Detection and Loop Initiation Stock solutions of sample containing different concentration of target DNA CCTCAACGTTAGCTTCACCAA 5'-3' (SEQ ID NO: 11), IOP/MB complex, inactivated amplifying agents 2 and 3, inactivated reporter SOSG were prepared in pH 7.4 TE buffer with 0.05% Tween80.

To detect the amplified signal from the inactivated reporter, a mixture of 5 μL of the IOP/MB complex (2.91 wt %) and 45 μL of sample solution containing target DNA of certain concentration was mixed and shaken for 15 min. IOP was then removed by magnet and the supernatant was mixed with 5 µL of the inactivated amplifying agent 2 (50 µM). A LED array of 690 nm light emission (30 W) was used to irradiate the solution for first 5 min. Then LED arrays of 500 nm light emission (10 W) was used to irradiate the solution simultaneously with that of 690 nm for the next 3 min. 5 µL of the inactivated reporter SOSG (100 µM) was added to the solution. Irradiation of 500 and 690 nm was continued for another 1 min. 50 µL of the solution was then transferred to a 384-well plate for fluorescence detection with excitation at 495 nm and fluorescence collected at 535 nm.

To directly detect the amplified signal from the inactivated amplifying agent, a mixture of 5 µL of the IOP/MB complex (2.91 wt %) and 45 µL of sample solution containing target DNA of certain concentration was mixed and shaken for 15 min. IOP was then removed by magnet and the supernatant was mixed with 5 µL of the inactivated amplifying agent 3 (100 µM). A LED array of 690 nm light emission (30 W) was used to irradiate the solution for first 5 min. Then LED arrays of 500 nm light emission (10 W) was used to irradiate the solution simultaneously with that of 690 nm for the next 3 min. 50 µL of the solution was then transferred to a 384-well plate for fluorescence detection with excitation at 495 nm and fluorescence collected at 535 nm.

Example 6—Comparison of Direct Detection and Autocatalytic Relay Loop Amplification with or without Reporter After further optimization of the molar ratio of each component and the irradiation time for exciting the amplifying agent and reporter, different detection modes were compared in terms of the fluorescence intensity generated by the inactivated reporter SOSG by various amount of $DNA_R$-MB. The LOD and LOQ of different detection methods were compared, where LOD was defined as the concentration at which the corresponding signal is equivalent to three folds of the standard deviation of the blank and LOQ was defined as that of ten folds of the standard deviation of the blank.

Figure 18:
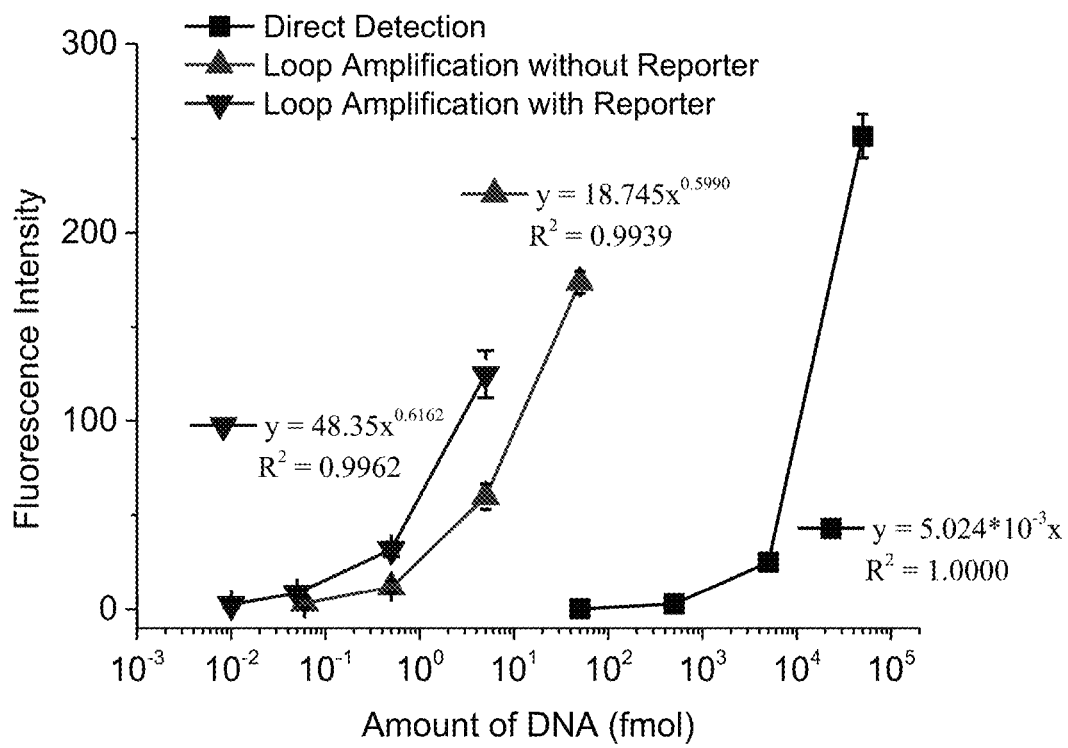
FIG. 18 depicts the fluorescence intensity generated by different amount of target DNA using direct detection of DNA-MB (square) and autocatalytic relay loop amplification with (down triangle) or without (up triangle) reporter.

The results are summarized in FIG. 18. With the current detection setup using 50 µL solution in a 384-well microplate in a Thermo Varioskan Flash microplate reader, the LOD and LOQ of direct detection of the commercially available fluorescein-labelled DNA could only be up to ca. 860 fmol (17 nM) and ca. 2.9 pmol (58 nM), respectively. However, for the autocatalytic relay loop amplification, after the autocatalytic amplification of the inactivated amplifying agent 2 to increase the amount of the available photosensitizers to activate the reporter probe SOSG, equal amount of DNAc-MB conjugate could lead to a much higher fluorescence signal. The autocatalytic relay loop amplified detection can enhance the LOD and LOQ to be 0.020 fmol (0.40 pM) and 0.14 fmol (2.8 pM). These showed a ca. 43000-fold improvement in LOD and a ca. 20000-fold improvement in LOQ. The loop amplification and detection could also be performed without using reporter probe SOSG by using inactivated amplifying agent 3 alone. With the intrinsic fluorescence of the activated form of 3, direct detection of its fluorescence is accurate and reliable enough that the addition of reporter probe SOSG is not necessary. This simplified the procedure and reduced the time needed for the detection process. However, as its fluorescence is weaker than that of SOSG, the detection based on the former would be less sensitive than the latter. The trade-off would be a ca. 4-fold decrease in LOD (0.087 fmol, 1.7 pM) and LOQ (0.65 fmol, 13 pM) compared to the detection performed with the combination of 2 and SOSG, while it was still 10000-fold and 4400-fold more sensitive than the LOD and LOQ of the detection performed with commercially available fluorescein.

Figure 19:
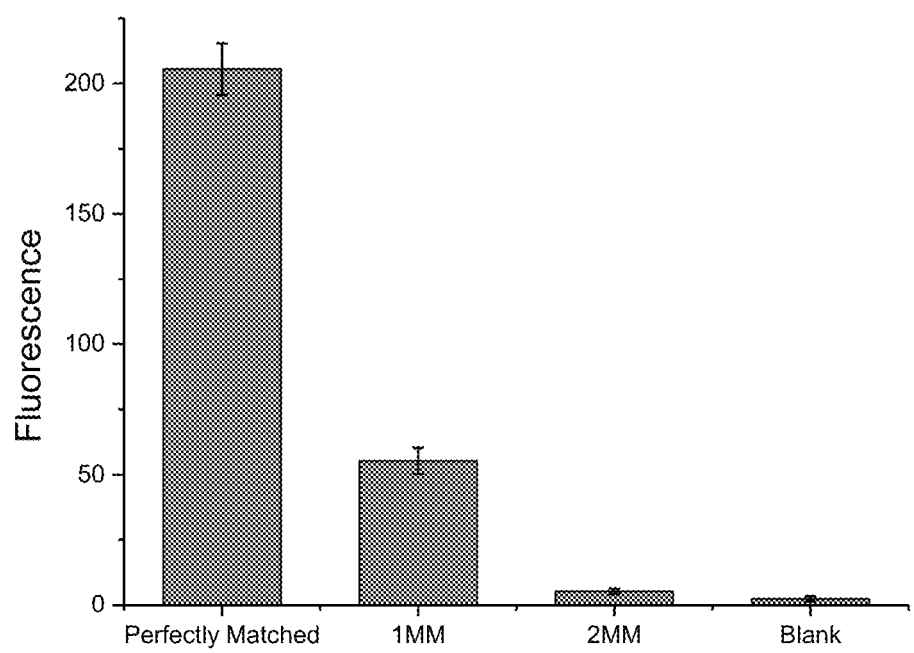
FIG. 19 depicts the fluorescence intensity generated by 1 nM of target DNAs with perfectly matched (SEQ ID NO: 11), one mismatched (SEQ ID NO: 12), or two mismatched (SEQ ID NO: 13) sequences using autocatalytic relay loop amplification.

Example 7—Comparison of the Specificity of Autocatalytic Relay Loop Amplification in the Presence of One or Two Base-Pair Mismatches The selectivity of the amplification method was investigated by comparing the fluorescence intensity of the reporter probe generated from using target DNA sequences with perfectly matching bases (SEQ ID NO: 11), a one mismatch (1 MM, SEQ ID NO: 12), and a two mismatch (2 MM, SEQ ID NO: 13), respectively. 1 nM of the above DNA sequences underwent the same amplification loop in Example 5 respectively and the results are summarized in FIG. 19. The fluorescence intensity of the amplification loop with the perfectly matched sequence was the highest among all the trials. While the 1 MM showed a 3-fold decrease in fluorescence comparing to the perfectly matched sequence, the fluorescence from the 2 MM sequence dropped to the level similar to the blank control. This suggests the method is of high selectivity to the sequence of DNA used.

Example 8—Exemplary Pathogen Specific DNA Targeting Sequences

Figure 20:
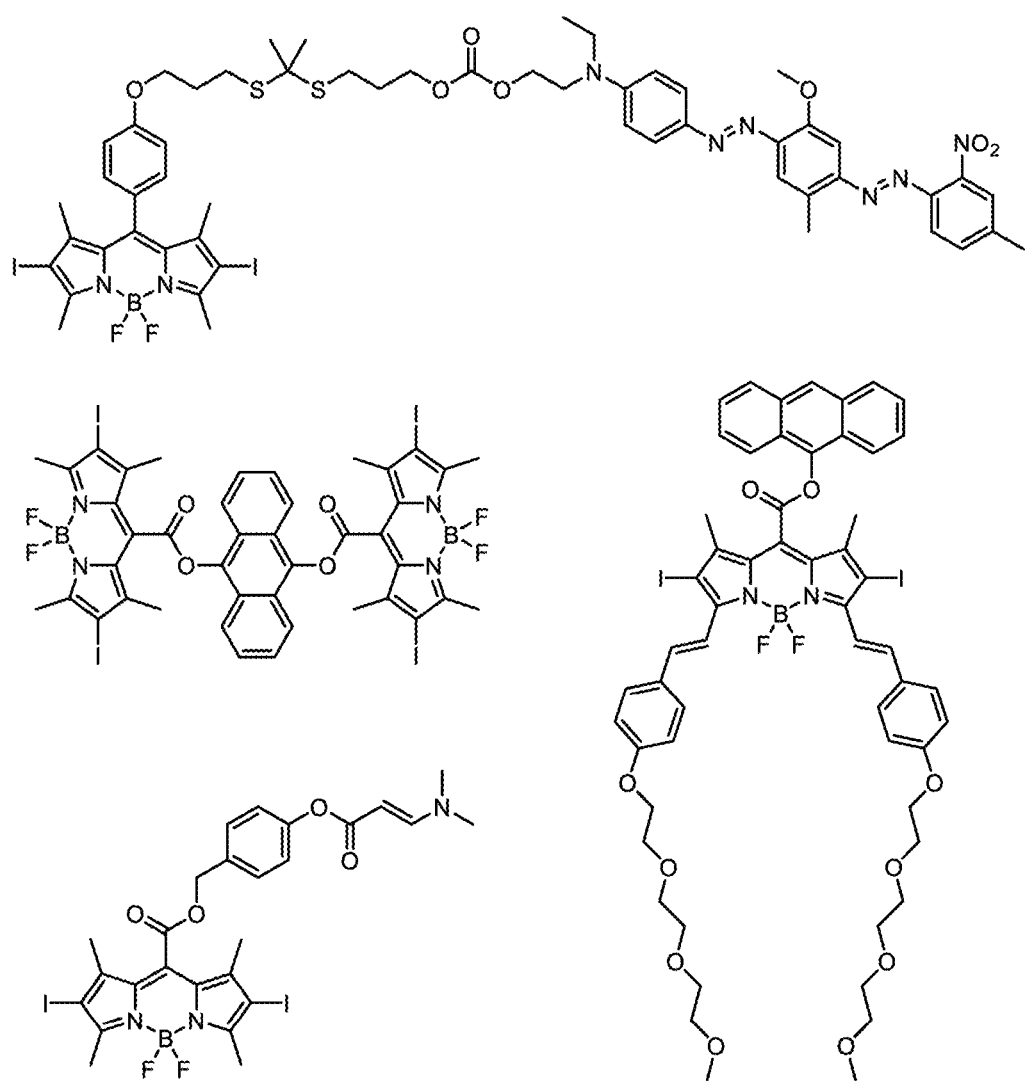
FIG. 20 depicts exemplary amplifying agents useful in certain embodiments of the methods described herein.

More DNA sequence and inactivated amplifying agents (Table 1 and FIG. 20) will be tested to examine the versatility of the relay loop amplification system.

TABLE 1

DNA sequences for detection of diseases

| Target DNA Origin | | DNA Targeting Sequence (5'-3') |
|---|---|---|
| Hepatitis B virus | Target 1 | TCA CCA TAT TCT TGG GAA CAA GA (SEQ ID NO: 5) |
| | Target 2 | CGA ACC ACT GAA CAA ATG GC (SEQ ID NO: 6) |
| M. Tuberculosis | Target 1 | CCT GCG AGC GTA GGC GTC GG (SEQ ID NO: 7) |
| | Target 2 | CTC GAC CTG AAA GAC GTT ATC C (SEQ ID NO: 8) |

TABLE 1-continued

DNA sequences for detection of diseases

| Target DNA Origin | | DNA Targeting Sequence (5'-3') |
|---|---|---|
| SARS-CoV-2 | Target 1 | GAC CCC AAA ATC AGC GAA AT (SEQ ID NO: 9) |
| | Target 2 | TTA CAA ACA TTG CCC GCA AA (SEQ ID NO: 10) |

What is claimed:

1. A method for detecting an analyte in a sample suspected of containing the analyte, the method comprising:
   (a) providing a conjugate substrate complex, wherein the conjugate substrate complex comprises a substrate comprising a plurality of targeting moieties bound via an optional first linker to a surface of the substrate; and a plurality of conjugates, wherein each of the plurality of conjugates comprises a releasing moiety covalently bonded via an optional second linker to a signal initiating agent, wherein each of the releasing moieties is reversibly bound to at least one of the plurality of targeting moieties and each of the plurality of targeting moieties is capable of selectively binding the analyte;
   (b) providing a plurality of inactivated amplifying agents, wherein each inactivated amplifying agents comprises a masking group and an amplifying agent;
   (c) providing a plurality of inactivated reporters;
   (d) contacting the conjugate substrate complex and the sample, wherein in the presence of the analyte, one or more of the plurality of targeting moieties bind to the analyte causing the release of one or more of the plurality of conjugates from the conjugate substrate complex thereby forming one or more unbound conjugates;
   (e) exciting the one or more unbound conjugates with a first excitation means whereby excitation of each of the one or more unbound the conjugate induces the signal initiating agent to emit an initiating signal;
   (f) exposing a first inactivated amplifying agent to the initiating signal, whereby exposure of the first inactivated amplifying agent to the initiating signal induces at least one transformation selected from the group consisting of cleavage, chemical transformation, and electrical transformation of at least one of the first inactivated amplifying agent or the masking group from the first inactivated amplifying agent thereby forming the first amplifying agent;
   (g) exciting the first amplifying agent with a second excitation means whereby excitation of the first amplifying agent induces the first amplifying agent to emit a relay signal, wherein the relay signal optionally induces at least one transformation selected from the group consisting of cleavage, chemical transformation, and electrical transformation of at least one of another inactivated amplifying agent or the masking group of another masked amplifying agent;
   (h) repeating step (g) one or more times thereby forming a plurality of relay signals;
   (i) exposing the plurality of inactivated reporters to the plurality of relay signals whereby exposure of the plurality inactivated reporters to the plurality of relay signals forms a plurality of activated reporters;
   (j) exciting the plurality of activated reporters thereby emitting an amplified reporting signal;
   (k) detecting the amplified reporting signal using a detection means; and
   (l) determining based on the amplified reporting signal if the analyte is detected in the sample,
   wherein the first excitation means and the second excitation means are the same or different;
   wherein the initiating signal and the relay signal are the same or different; and wherein the analyte is deoxyribonucleic acid (DNA), ribonucleic acid (RNA), a peptide nucleic acid (PNA), an antibody, an antibody fragment, a peptide, a protein, or a small molecule.

2. The method of claim 1, wherein exposure of the first inactivated amplifying agent to the initiating signal induces the cleavage of the masking group.

3. The method of claim 1, wherein step (g) is repeated more than 100 times.

4. The method of claim 1, wherein each of the plurality of targeting moieties comprises a deoxyribonucleic acid (DNA), ribonucleic acid (RNA), a peptide nucleic acid (PNA), an antibody, an antibody fragment, a peptide, a protein, or a small molecule.

5. The method of claim 1, wherein the signal initiating agent comprises a photosensitizer, a nanoparticle, a protein, a luminescent agent, or a fluorescent agent.

6. The method of claim 1, wherein the initiating signal and the relay signal are the same and selected from the group consisting of a small molecule, heat, light, or a combination thereof.

7. The method of claim 1, wherein each of the initiating signal and the relay signal are singlet oxygen.

8. The method of claim 1, wherein each of the plurality of conjugates comprise DNA, RNA, PNA, an antibody, an antibody fragment, a peptide, a protein, a small molecule, or a metal complex.

9. The method of claim 1, wherein each of the plurality of targeting moieties comprises a single stranded DNA sequence and each of the plurality of releasing moieties comprise a substantially complimentary single stranded DNA sequence; or each of the plurality of targeting moieties comprise a single stranded RNA sequence and each of the plurality of releasing moieties each comprise a substantially complimentary single stranded RNA sequence.

10. The method of claim 1, wherein the targeting moiety is covalently bonded via a first linker to the substrate, wherein the linker comprises a first nucleotide spacer comprising a first single stranded DNA spacer sequence or a first single stranded RNA spacer sequence.

11. The method of claim 10, wherein the first DNA spacer sequence or the first single stranded RNA spacer sequence is between 2-10 nucleotides.

12. The method of claim 1, wherein the signal initiating agent comprises a photosensitizer.

13. The method of claim 12, wherein the plurality of conjugates are selected from the group consisting of:

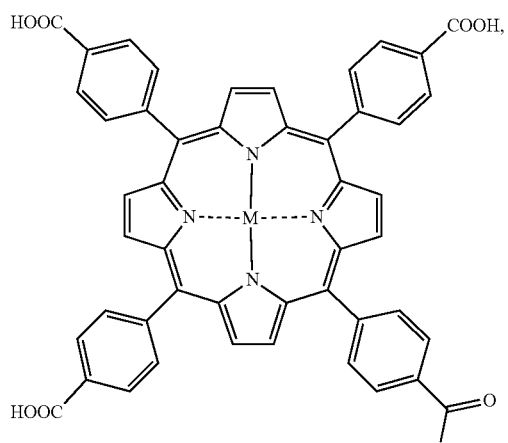

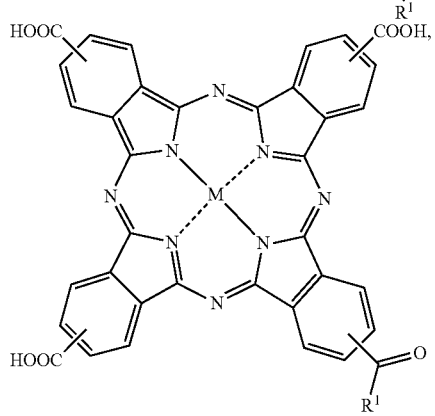

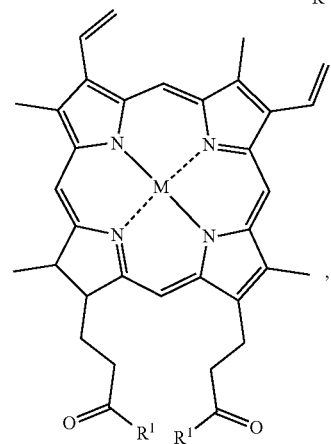

-continued

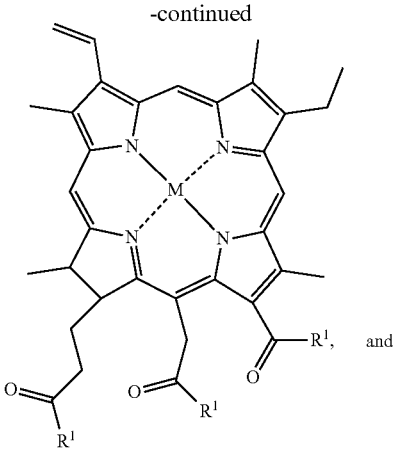

or a salt thereof, wherein $R^1$ is —X—Y or OH, wherein X is the linker, M is 2H or a non-paramagnetic metal, and Y is the releasing moiety, with the proviso that only one $R^1$ is —X—Y.

14. The method of claim 12, wherein each of the initiating signal, the relay signal, and the plurality of relay signals is singlet oxygen.

15. The method of claim 12, wherein the plurality of inactivated amplifying agents is selected from the group consisting of:

-continued

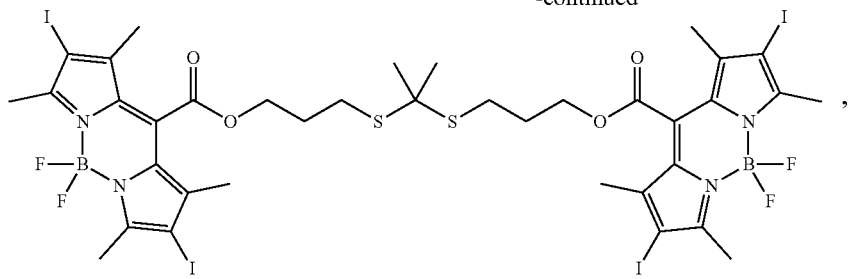

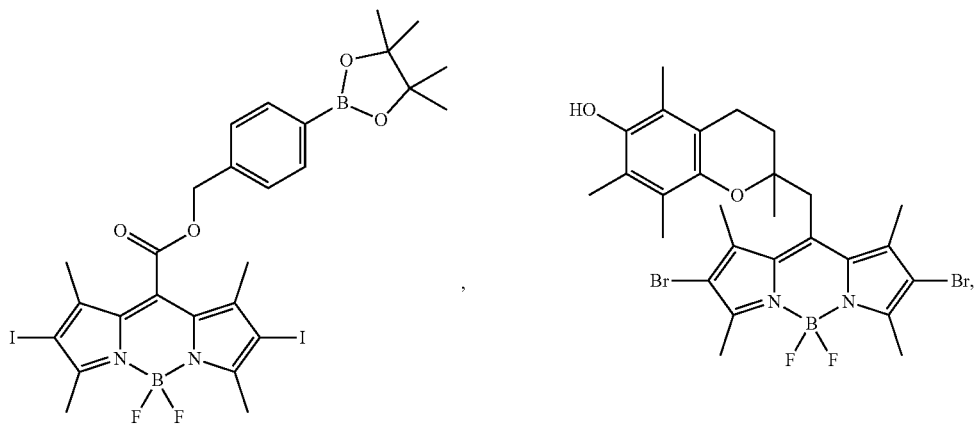

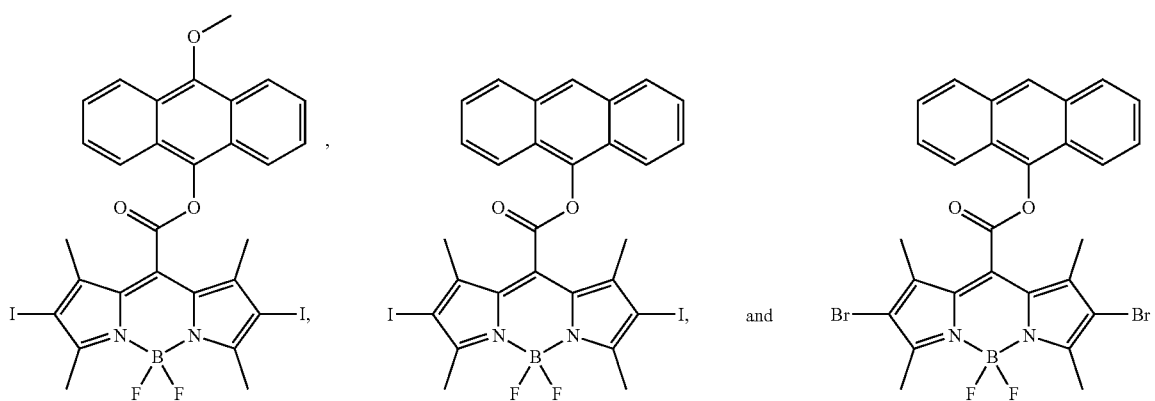

or a salt thereof.

16. The method of claim 12, wherein the plurality of inactivated reporters have the structure:

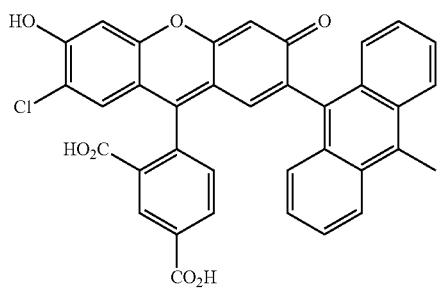 [SMILES: Cc1c2ccccc2c(-c2cc3c(-c4ccc(C(=O)O)cc4C(=O)O)c4cc(Cl)c(O)cc4oc-3cc2=O)c2ccccc12]

or a salt thereof.

17. A method for detecting a DNA analyte in a sample suspected of containing the DNA analyte, the method comprising:

(a) providing a conjugate substrate complex, wherein the conjugate substrate complex comprises a substrate comprising a plurality of DNA sequence targeting moieties bound via a first linker to a surface of the substrate; and a plurality of DNA conjugates, wherein each of the plurality of DNA conjugates comprise a conjugating DNA sequence moiety covalently bonded via a second linker to a photosensitizer, wherein each of the DNA sequence releasing moieties is reversibly bound to one of the plurality of DNA sequence targeting moieties and each of the plurality of DNA sequence targeting moieties is capable of selectively binding the analyte;

(b) providing a plurality of inactivated amplifying agents selected from the group consisting of:

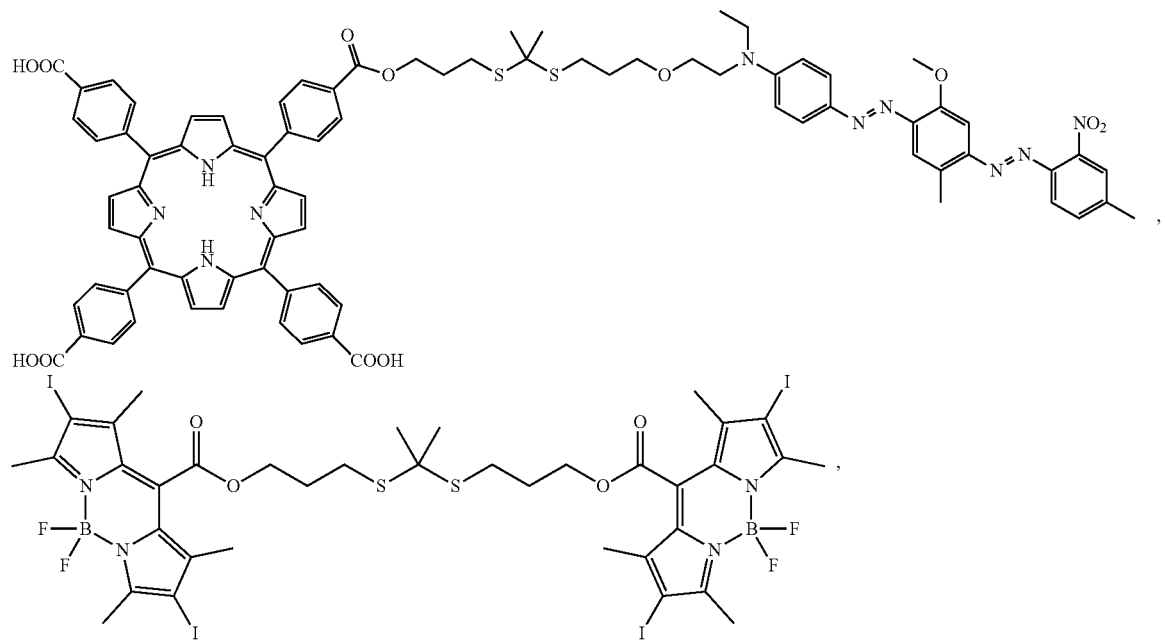
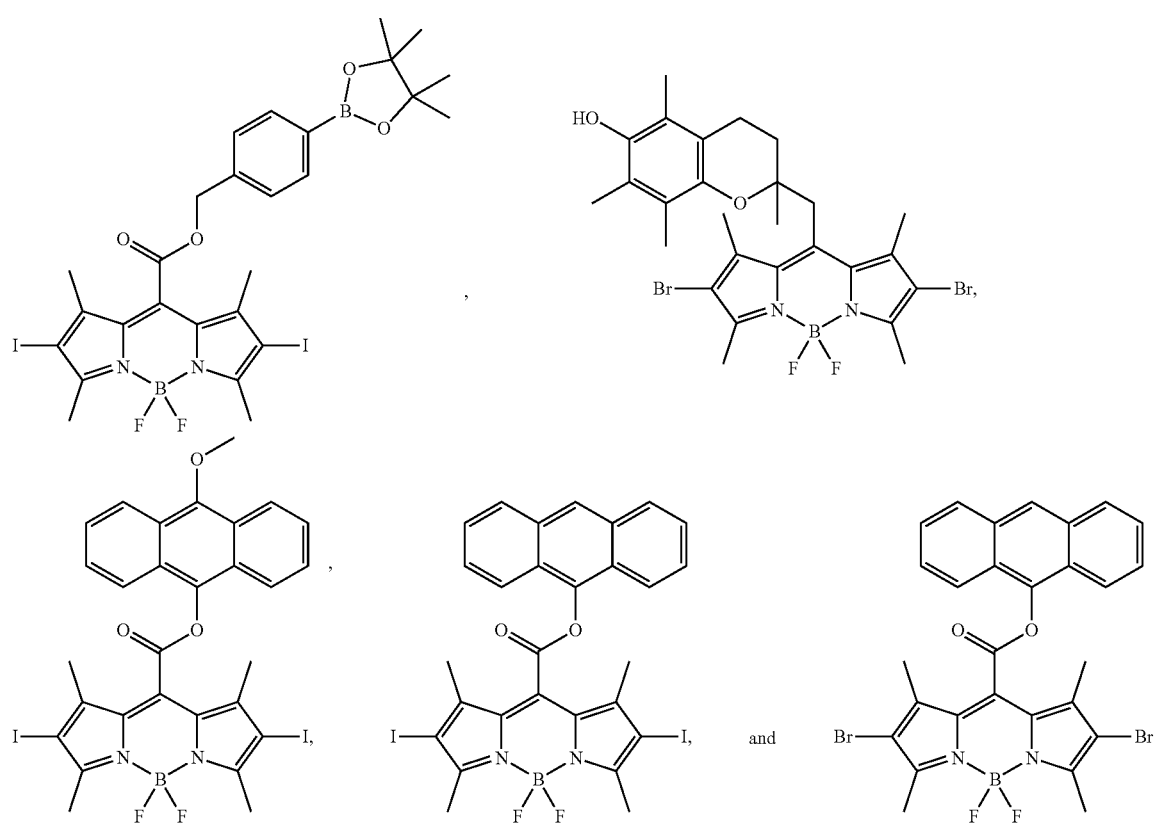
or a salt thereof, wherein each inactivated amplifying agent comprises a masking group and an amplifying agent;

(c) providing a plurality of inactivated reporters having the formula:

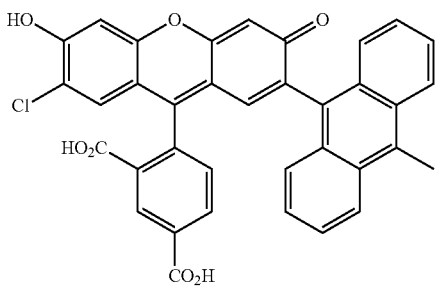 [SMILES: Cc1c2ccccc2c(-c2cc3c(-c4ccc(C(=O)O)cc4C(=O)O)c4cc(Cl)c(O)cc4oc-3cc2=O)c2ccccc12]

or a salt thereof;
(d) contacting the conjugate substrate complex and the sample, wherein in the presence of the analyte, one or more of the plurality of DNA sequence targeting moieties binds to the DNA analyte causing the release of one or more of the plurality of DNA conjugates from the conjugate substrate complex thereby forming one or more unbound DNA conjugates;
(e) irradiating the one or more unbound DNA conjugates with a first wavelength of light in the presence of triplet oxygen thereby producing singlet oxygen;
(f) exposing a first inactivated amplifying agent to the singlet oxygen, whereby exposure of the first inactivated amplifying agent to the singlet oxygen induces the cleavage of the masking group from the first inactivated amplifying agent thereby forming the first amplifying agent;
(g) irradiating the first amplifying agent with a second wavelength of light in the presence of triplet oxygen thereby producing singlet oxygen, wherein the amplified singlet oxygen optionally induces the release of the masking group of another masked amplifying agent;
(h) repeating step (g) one or more times thereby forming a plurality of singlet oxygen;
(i) exposing the plurality of inactivated reporters to the plurality of singlet oxygen whereby exposure of the plurality inactivated reporters to the plurality of singlet oxygen forms a plurality of activated reporters having the structure:

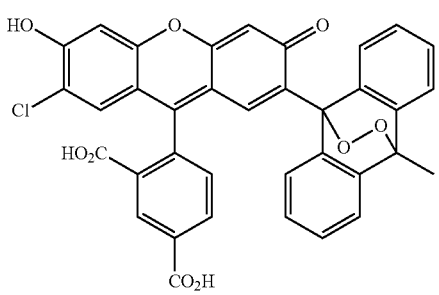 [SMILES: CC12OOC(c3cc4c(-c5ccc(C(=O)O)cc5C(=O)O)c5cc(Cl)c(O)cc5oc-4cc3=O)(c3ccccc31)c1ccccc12]

or a salt thereof;

j) irradiating the plurality of activated reporters with visible light thereby emitting an amplified reporting signal;
(k) detecting the amplified reporting signal using a spectrometer; and
(l) determining based on the amplified reporting signal if the analyte is detected in the sample.

18. The method of claim 17, wherein the photosensitizer comprises a porphyrin, a phthalocyanine, a chlorin, a bacteriochlorin, a phenothiazinium, a xanthene, methylene blue, or a boron dipyrromethene (BODIPY).

19. The method of claim 17, wherein each of the plurality of DNA conjugates has the formula:

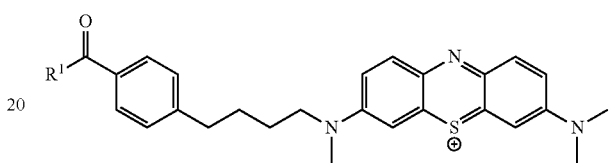

or a salt thereof, wherein $R^1$ is —X—Y or OH, wherein X is the linker and Y is the releasing moiety.

20. The method of claim 17, wherein each of the plurality of DNA conjugates has the formula:

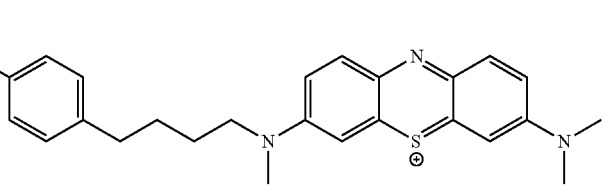

or a conjugate salt thereof, wherein m is a whole number selected from 0-2, n is a whole number selected from 3-5; J for each instance is a nucleotide independently selected from the group consisting of A, C, G, and T; and Q is the releasing moiety.

21. The method of claim 20, wherein m is 0; N is 4; and each J is A.

22. The method of claim 20, wherein the plurality of inactivated amplifying agents each have the structure:

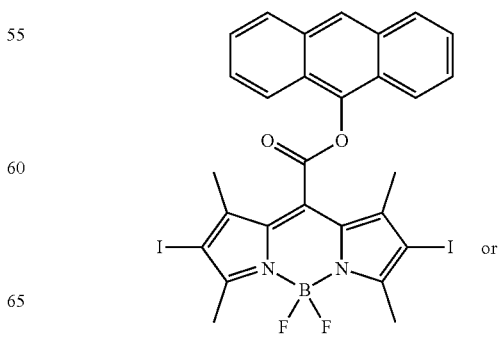

-continued

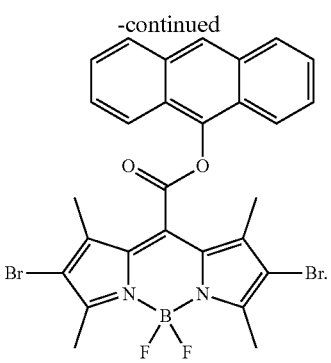

23. The method of claim 17, wherein each of the plurality of DNA sequence targeting moieties comprises a polynucleotide sequence selected from the group consisting of: SEQ ID NO: 5, SEQ ID NO: 6, SEQ ID NO: 7, SEQ ID NO: 8, SEQ ID NO: 9, and SEQ ID NO: 10; and optionally a nucleotide spacer having between 2-10 nucleotides.

24. A method for detecting an analyte in a sample suspected of containing the analyte, the method comprising:
(a) providing a conjugate substrate complex, wherein the conjugate substrate complex comprises a substrate comprising a plurality of releasing moieties bound via an optional first linker to a surface of the substrate; and a plurality of conjugates, wherein each of the plurality of conjugates comprises a targeting moiety covalently bonded via an optional second linker to a signal initiating agent, wherein each of the targeting moieties is reversibly bound to at least one of the plurality of releasing moieties and each of the plurality of targeting moieties is capable of selectively binding the analyte;
(b) providing a plurality of inactivated amplifying agents, wherein each inactivated amplifying agents comprises a masking group and an amplifying agent;
(c) providing a plurality of inactivated reporters;
(d) contacting the conjugate substrate complex and the sample, wherein in the presence of the analyte, one or more of the of targeting moieties bind to the analyte causing the release of one or more of the plurality of conjugates from the conjugate substrate complex thereby forming one or more unbound conjugates;
(e) exciting the one or more unbound conjugates with a first excitation means whereby excitation of each of the one or more unbound the conjugate induces the signal initiating agent to emit an initiating signal;
(f) exposing a first inactivated amplifying agent to the initiating signal, whereby exposure of the first inactivated amplifying agent to the initiating signal induces at least one transformation selected from the group consisting of cleavage, chemical transformation, and electrical transformation of at least one of the first inactivated amplifying agent or the masking group from the first inactivated amplifying agent thereby forming the first amplifying agent;
(g) exciting the first amplifying agent with a second excitation means whereby excitation of the first amplifying agent induces the first amplifying agent to emit a relay signal, wherein the relay signal optionally induces at least one transformation selected from the group consisting of cleavage, chemical transformation, and electrical transformation of at least one of another inactivated amplifying agent or the masking group of another masked amplifying agent;
(h) repeating step (g) one or more times thereby forming a plurality of relay signals;
(i) exposing the plurality of inactivated reporters to the plurality of relay signals whereby exposure of the plurality inactivated reporters to the plurality of relay signals forms a plurality of activated reporters;
(j) exciting the plurality of activated reporters thereby emitting an amplified reporting signal;
(k) detecting the amplified reporting signal using a detection means; and
(l) determining based on the amplified reporting signal if the analyte is detected in the sample,
wherein the first excitation means and the second excitation means are the same or different;
wherein the initiating signal and the relay signal are the same or different; and wherein the analyte is deoxyribonucleic acid (DNA), ribonucleic acid (RNA), a peptide nucleic acid (PNA), an antibody, an antibody fragment, a peptide, a protein, or a small molecule.

25. The method of claim 24, wherein each of the plurality of conjugates is selected from the group consisting of:

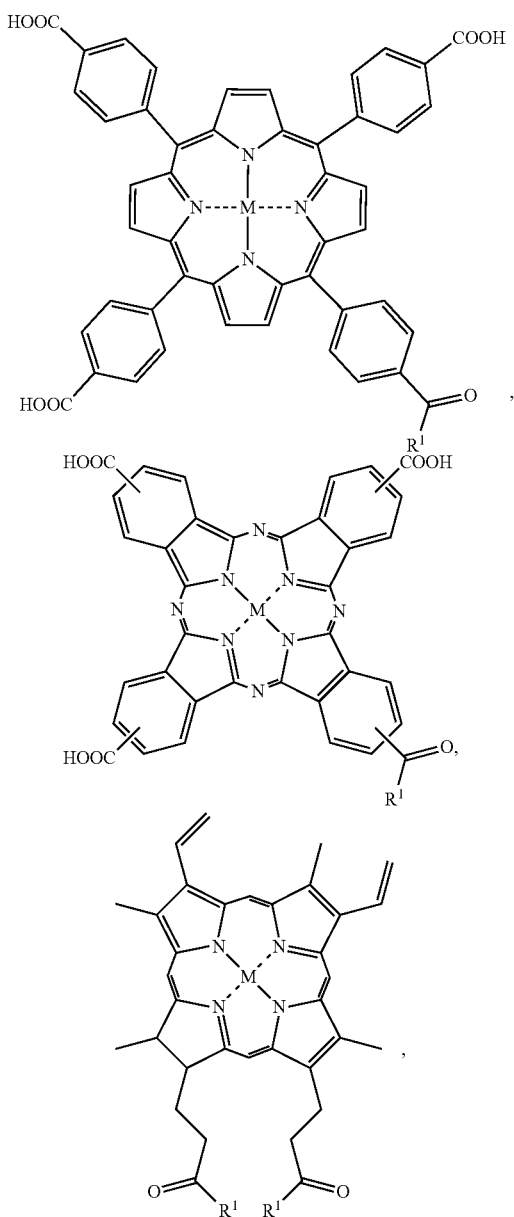

-continued
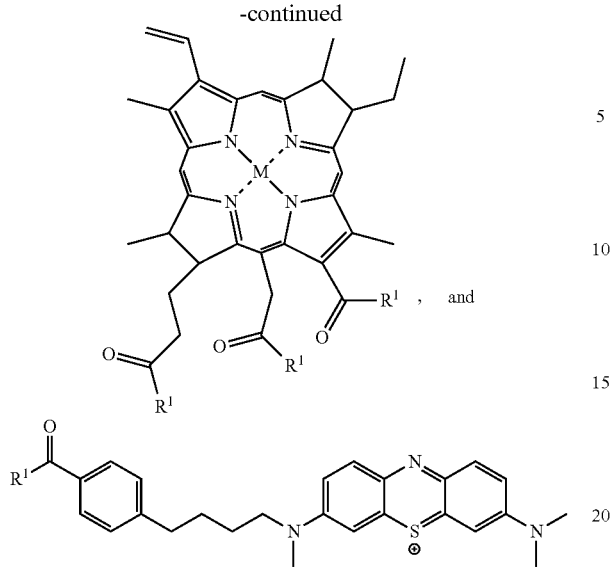
or a salt thereof, wherein $R^1$ is —X—$Y^1$ or OH, wherein X is the linker, M is 2H or a non-paramagnetic metal, and $Y^1$ is the targeting moiety, with the proviso that only one $R^1$ is —X—$Y^1$.
* * * * *

SEQUENCE LISTING

<160> NUMBER OF SEQ ID NOS: 13

<210> SEQ ID NO 1
<211> LENGTH: 17
<212> TYPE: DNA
<213> ORGANISM: Artificial Sequence
<220> FEATURE:
<223> OTHER INFORMATION: Releasing DNA Sequence + 5A DNA Spacer;
      Synthesized in Lab

<400> SEQUENCE: 1
cctcaacgtt agaaaaa                                                17

<210> SEQ ID NO 2
<211> LENGTH: 26
<212> TYPE: DNA
<213> ORGANISM: Artificial Sequence
<220> FEATURE:
<223> OTHER INFORMATION: Targeting DNA Sequence + 5A DNA Spacer;
      Synthesized in Lab

<400> SEQUENCE: 2
ttggtgaagc taacgttgag gaaaaa                                      26

<210> SEQ ID NO 3
<211> LENGTH: 21
<212> TYPE: DNA
<213> ORGANISM: Artificial Sequence
<220> FEATURE:
<223> OTHER INFORMATION: Targeting DNA; Synthesized in Lab

<400> SEQUENCE: 3
ttggtgaagc taacgttgag g                                           21

<210> SEQ ID NO 4
<211> LENGTH: 12
<212> TYPE: DNA
<213> ORGANISM: Artificial Sequence
<220> FEATURE:
<223> OTHER INFORMATION: Releasing DNA; Synthesized in Lab

<400> SEQUENCE: 4
cctcaacgtt ag                                                     12

<210> SEQ ID NO 5
<211> LENGTH: 23
<212> TYPE: DNA
<213> ORGANISM: Hepatitis B virus

<400> SEQUENCE: 5
tcaccatatt cttgggaaca aga                                         23

<210> SEQ ID NO 6
<211> LENGTH: 20

-continued

```
<212> TYPE: DNA
<213> ORGANISM: Hepatitis B virus

<400> SEQUENCE: 6
cgaaccactg aacaaatggc                                              20

<210> SEQ ID NO 7
<211> LENGTH: 20
<212> TYPE: DNA
<213> ORGANISM: Mycobacterium tuberculosis

<400> SEQUENCE: 7
cctgcgagcg taggcgtcgg                                              20

<210> SEQ ID NO 8
<211> LENGTH: 22
<212> TYPE: DNA
<213> ORGANISM: Mycobacterium tuberculosis

<400> SEQUENCE: 8
ctcgacctga aagacgttat cc                                           22

<210> SEQ ID NO 9
<211> LENGTH: 20
<212> TYPE: DNA
<213> ORGANISM: Severe Acute Respiratory Syndrome Coronavirus 2

<400> SEQUENCE: 9
gaccccaaaa tcagcgaaat                                              20

<210> SEQ ID NO 10
<211> LENGTH: 20
<212> TYPE: DNA
<213> ORGANISM: Severe Acute Respiratory Syndrome Coronavirus 2

<400> SEQUENCE: 10
ttacaaacat tggccgcaaa                                              20

<210> SEQ ID NO 11
<211> LENGTH: 21
<212> TYPE: DNA
<213> ORGANISM: Artificial Sequence
<220> FEATURE:
<223> OTHER INFORMATION: Target Analyte DNA Sequence; Synthesized in Lab

<400> SEQUENCE: 11
cctcaacgtt agcttcacca a                                            21

<210> SEQ ID NO 12
<211> LENGTH: 21
<212> TYPE: DNA
<213> ORGANISM: Artificial Sequence
<220> FEATURE:
<223> OTHER INFORMATION: Target Analyte DNA Sequence with 1 Mismatach;
      Synthesized in Lab

<400> SEQUENCE: 12
cctcaacgtt cgcttcacca a                                            21

<210> SEQ ID NO 13
<211> LENGTH: 21
<212> TYPE: DNA
<213> ORGANISM: Artificial Sequence
<220> FEATURE:
<223> OTHER INFORMATION: Target Analyte DNA Sequence with 2 Mismatach;
```

```
       Synthesized in Lab

<400> SEQUENCE: 13
cctaaacgtt cgcttcacca a                                              21
```